(12) United States Patent
Nemoto

(10) Patent No.: US 7,695,457 B2
(45) Date of Patent: Apr. 13, 2010

(54) SYRINGE BARREL WITH ROUGHENED SURFACE

(75) Inventor: Shigeru Nemoto, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 0 days.

(21) Appl. No.: 10/692,090

(22) Filed: Oct. 23, 2003

(65) Prior Publication Data

US 2004/0087910 A1    May 6, 2004

Related U.S. Application Data

(62) Division of application No. 09/780,731, filed on Feb. 9, 2001, now Pat. No. 6,676,635.

(30) Foreign Application Priority Data

| Feb. 2, 2000 | (JP) | ............................. 2001-026782 |
| Feb. 10, 2000 | (JP) | ............................. 2000-033520 |
| Feb. 15, 2000 | (JP) | ............................. 2000-037176 |
| Jun. 30, 2000 | (JP) | ............................. 2000-198358 |

(51) Int. Cl.
*A61M 37/00*   (2006.01)
*A61M 5/00*    (2006.01)
*A61M 5/315*   (2006.01)

(52) U.S. Cl. .................. 604/232; 604/227; 604/154

(58) Field of Classification Search ................ 604/131, 604/151, 110, 181, 187, 218, 232, 191, 188, 604/184, 195–199, 227, 154; 128/DIG. 1, 128/919
See application file for complete search history.

(56) References Cited

U.S. PATENT DOCUMENTS

| 3,253,592 | A | 6/1966 | Von Pechmann |
| 3,316,909 | A | 5/1967 | Cowley |
| 3,438,549 | A | 4/1969 | Ritz |
| 3,556,099 | A | 1/1971 | Knight et al. |
| 3,990,446 | A | 11/1976 | Taylor |
| 4,006,736 | A | 2/1977 | Kranys et al. |

(Continued)

FOREIGN PATENT DOCUMENTS

CH              366 634 A      1/1963

(Continued)

OTHER PUBLICATIONS

Office Action, dated Dec. 6, 2005, from corresponding European Patent Application Serial No. 01 400 344.6—1526.

(Continued)

*Primary Examiner*—Matthew F Desanto
(74) *Attorney, Agent, or Firm*—Knobbe Martens Olson & Bear, LLP

(57) ABSTRACT

Since this syringe has projections provided on the rear surface of a flange of a syringe barrel, when it is inserted in an insertion groove of a cylinder holder, the tips of projections are compressed and the flange is fixed. Consequently, even when a solution having high viscosity is injected at higher pressure, breakage does not occur easily. Further, pressure-receiving area may also be increased by providing a guide defining mounting direction of a syringe, alternatively, a positioning mechanism may be provided so as to obtain mounting at a correct position, or the surface of a flange may be roughened.

4 Claims, 33 Drawing Sheets

U.S. PATENT DOCUMENTS

| | | | |
|---|---|---|---|
| 4,030,498 A | 6/1977 | Tompkins | |
| 4,253,501 A | 3/1981 | Ogle | |
| 4,516,969 A | 5/1985 | Kintner | |
| 4,540,405 A | 9/1985 | Miller et al. | |
| 4,677,980 A | 7/1987 | Reilly et al. | |
| 4,718,463 A | 1/1988 | Jurgens, Jr. et al. | |
| 4,804,368 A * | 2/1989 | Skakoon et al. | 604/155 |
| 4,838,857 A | 6/1989 | Strowe et al. | |
| 4,941,879 A | 7/1990 | Butler et al. | |
| 5,188,599 A | 2/1993 | Botich et al. | |
| 5,226,897 A | 7/1993 | Nevens et al. | |
| 5,275,582 A * | 1/1994 | Wimmer | 604/218 |
| 5,300,031 A | 4/1994 | Neer | |
| 5,306,147 A | 4/1994 | Dragan et al. | |
| 5,306,157 A | 4/1994 | Francisco | |
| 5,322,511 A | 6/1994 | Armbruster et al. | |
| 5,383,858 A | 1/1995 | Reilly et al. | |
| 5,407,431 A * | 4/1995 | Botich et al. | 604/110 |
| 5,429,611 A | 7/1995 | Rait | |
| 5,535,746 A | 7/1996 | Hoover et al. | |
| 5,545,140 A | 8/1996 | Conero et al. | |
| 5,554,132 A | 9/1996 | Straits et al. | |
| 5,593,391 A | 1/1997 | Stanners | |
| 5,667,495 A | 9/1997 | Bitdinger et al. | |
| 5,722,956 A | 3/1998 | Sims et al. | |
| 5,792,102 A | 8/1998 | Müller-Spaäth | |
| 5,833,668 A | 11/1998 | Aguilar | |
| 5,873,499 A | 2/1999 | Leschinsky et al. | |
| 5,897,532 A | 4/1999 | Spallek et al. | |
| 5,925,032 A | 7/1999 | Clements | |
| 5,944,694 A | 8/1999 | Hitchins et al. | |
| 5,947,935 A | 9/1999 | Rhinehart et al. | |
| 5,997,502 A * | 12/1999 | Reilly et al. | 604/67 |
| 6,017,330 A | 1/2000 | Hitchins et al. | |
| 6,019,745 A | 2/2000 | Gray | |
| 6,117,112 A | 9/2000 | Mahurkar | |
| 6,296,625 B1 | 10/2001 | Vetter et al. | |
| 6,368,308 B1 | 4/2002 | Nerney | |
| 6,457,606 B1 | 10/2002 | Burke | |
| 6,569,127 B1 | 5/2003 | Fago et al. | |
| 6,676,635 B2 | 1/2004 | Nemoto | |
| 7,137,967 B2 | 11/2006 | Nemoto | |
| 7,264,612 B2 | 9/2007 | Nemoto | |
| 7,344,520 B2 | 3/2008 | Nemoto | |
| 7,393,341 B2 | 7/2008 | Nemoto | |
| 2001/0014996 A1* | 8/2001 | Ericson et al. | 24/136 R |
| 2001/0023336 A1* | 9/2001 | Nolan et al. | 604/152 |
| 2002/0165491 A1 | 11/2002 | Reilly | |
| 2003/0028102 A1 | 2/2003 | Nemoto | |
| 2003/0050607 A1 | 3/2003 | Gagnieux et al. | |
| 2004/0082919 A1 | 4/2004 | Nemoto | |
| 2004/0087909 A1 | 5/2004 | Nemoto | |
| 2008/0132845 A1 | 6/2008 | Nemoto | |
| 2008/0132853 A1 | 6/2008 | Nemoto | |

FOREIGN PATENT DOCUMENTS

| | | |
|---|---|---|
| DE | 91 05 980.1 | 8/1991 |
| EP | 0 208 975 | 1/1987 |
| EP | 0 384 657 A | 8/1990 |
| EP | 0 919 251 A2 | 6/1999 |
| GB | J24783 A | 10/1910 |
| GB | 2308302 A | 6/1997 |
| JP | 07 255748 | 10/1995 |
| JP | H07-310537 | 11/1995 |
| JP | 09 122234 A | 5/1997 |
| JP | H09-125600 | 5/1997 |
| JP | 10 137336 | 5/1998 |
| JP | 11 178923 | 7/1999 |

OTHER PUBLICATIONS

Office Action dated Oct. 17, 2005 and European Search Report dated Nov. 17, 2004 from related European Patent Application EP 04 076 413.6—1526.

Office Action dated Oct. 17, 2005 and European Search Report dated Nov. 17, 2004 from related European Patent Application EP 04 076 459.9—1526.

Office Action dated Oct. 7, 2005 and European Search Report dated Nov. 17, 2004 from related European Patent Application EP 04 076 550.5—1526.

Office Action dated Oct. 7, 2005 and European Search Report dated Nov. 17, 2004 from related European Patent Application EP 04 076 575.2—1526.

European Search Report dated Nov. 9, 2004 from corresponding European Patent Application EP 04 07 6459.9.

Office Action, dated Aug. 9, 2007, from corresponding Korean Patent Application No. 2007-48807.

Farfan, et. al., "Temporal code in the vibrissal system-Part II: Roughness surface discrimination," 16th Argentine Bioengineering Congress and the 5th Conference of Clinical Engineering, Journal of Physics: Conference Series (90), 2007.

Sheen, et. al. "Food Surface Texture Measurement Using Reflective Confocal Laser Scanning Microscopy," retrieved from the website: http://www.ars.usda.gov/research/publications/publications.htm?SEQ_NO_115=219013, Jul. 1, 2008.

Office Action in Japanese Application No. 2000-037176 dated Jun. 10, 2009.

Extended European Search Report issued in Application No. 08103395.3 on Jul. 22, 2009.

Official Communication in Japanese Application No. 2000-033520 dated Oct. 19, 2009.

Official Communication in Japanese Application No. 2000 198358 dated Nov. 4, 2009.

* cited by examiner

FIG.4
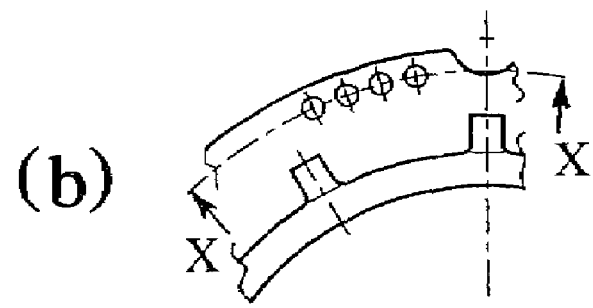
(b)
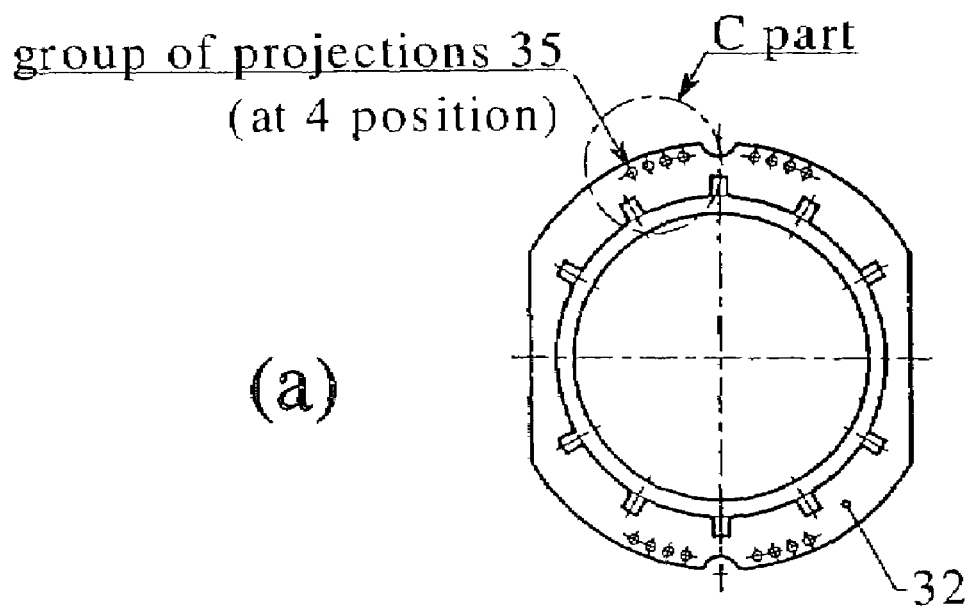
group of projections 35 (at 4 position)
C part
(a)
32
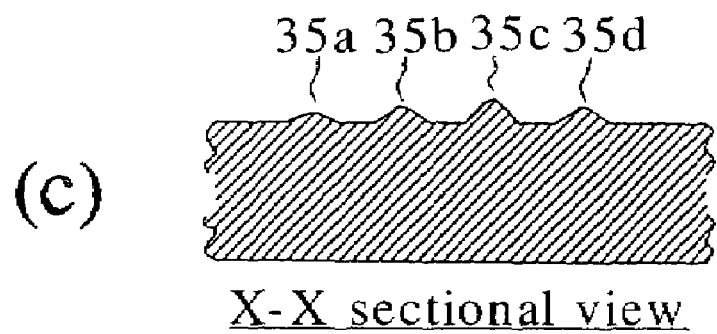
35a 35b 35c 35d
(c)
X-X sectional view

FIG.6
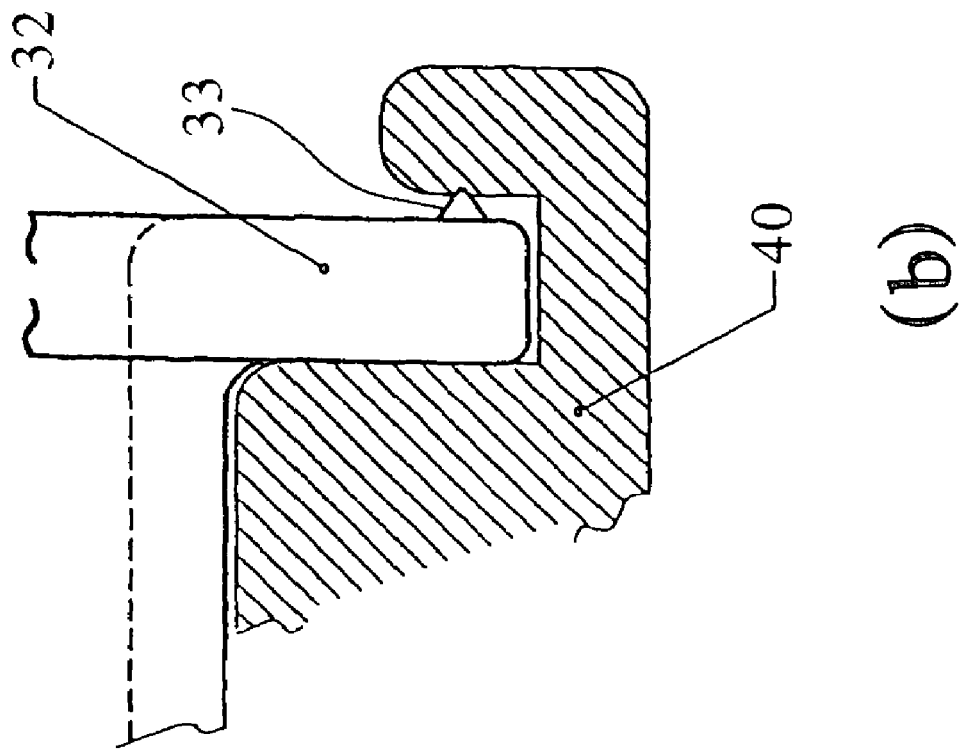
(b)
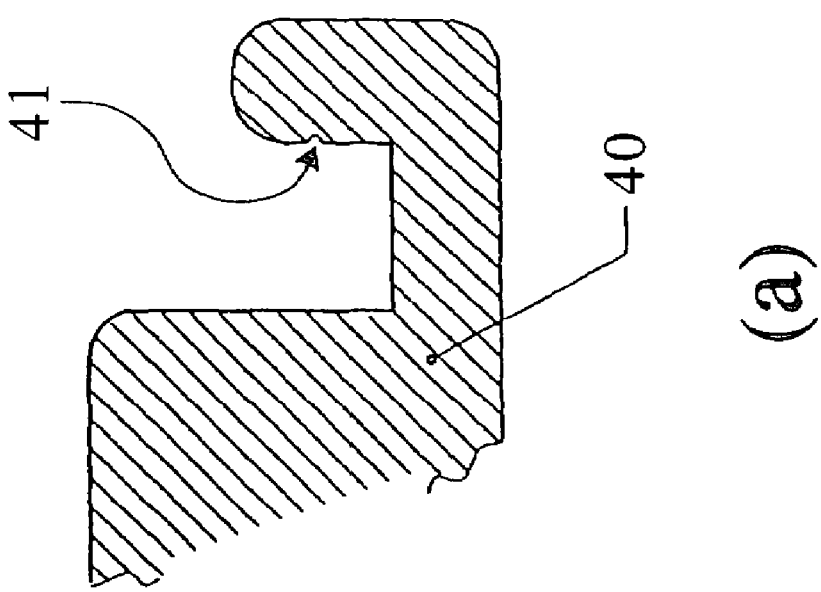
(a)

FIG.15
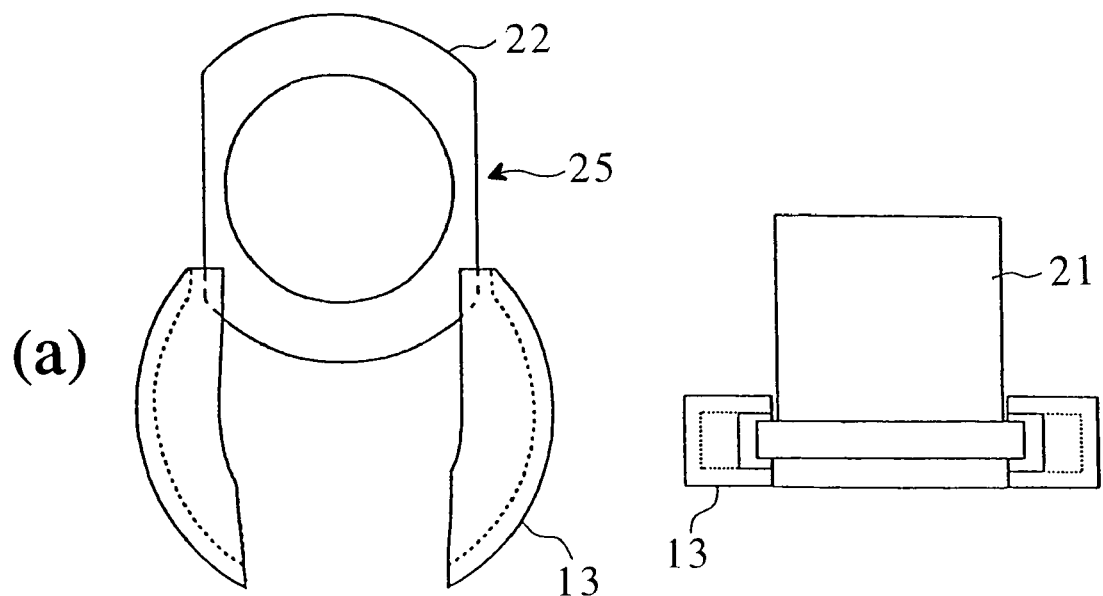
(a)
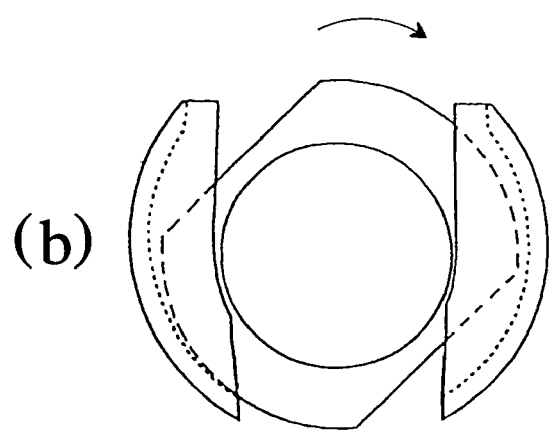
(b)
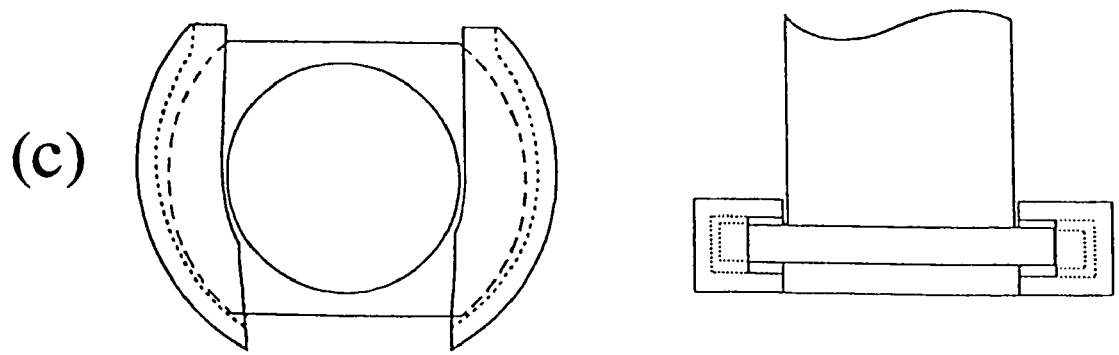
(c)

FIG. 19
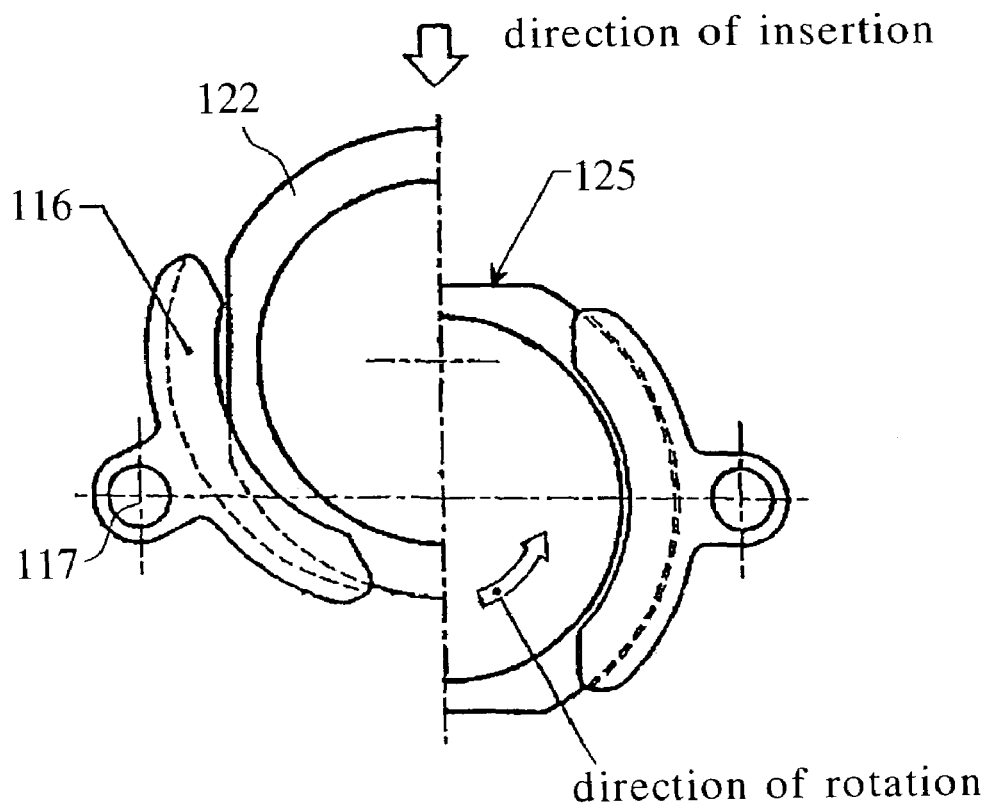
direction of insertion
direction of rotation
(a)　　　(b)
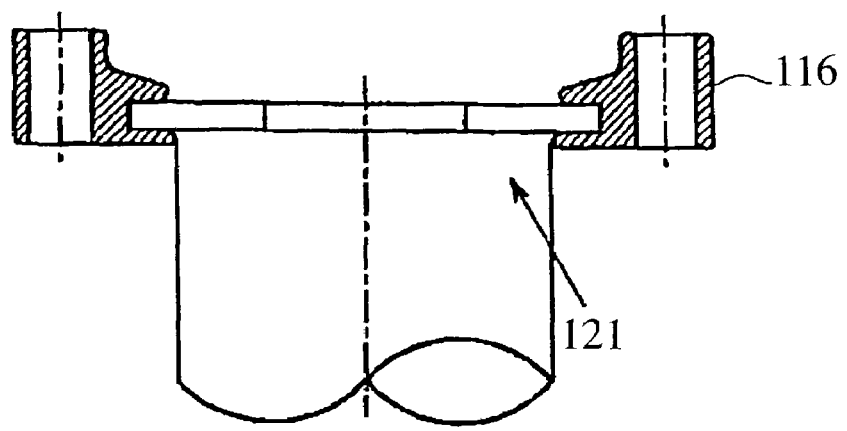
(c)

FIG.25
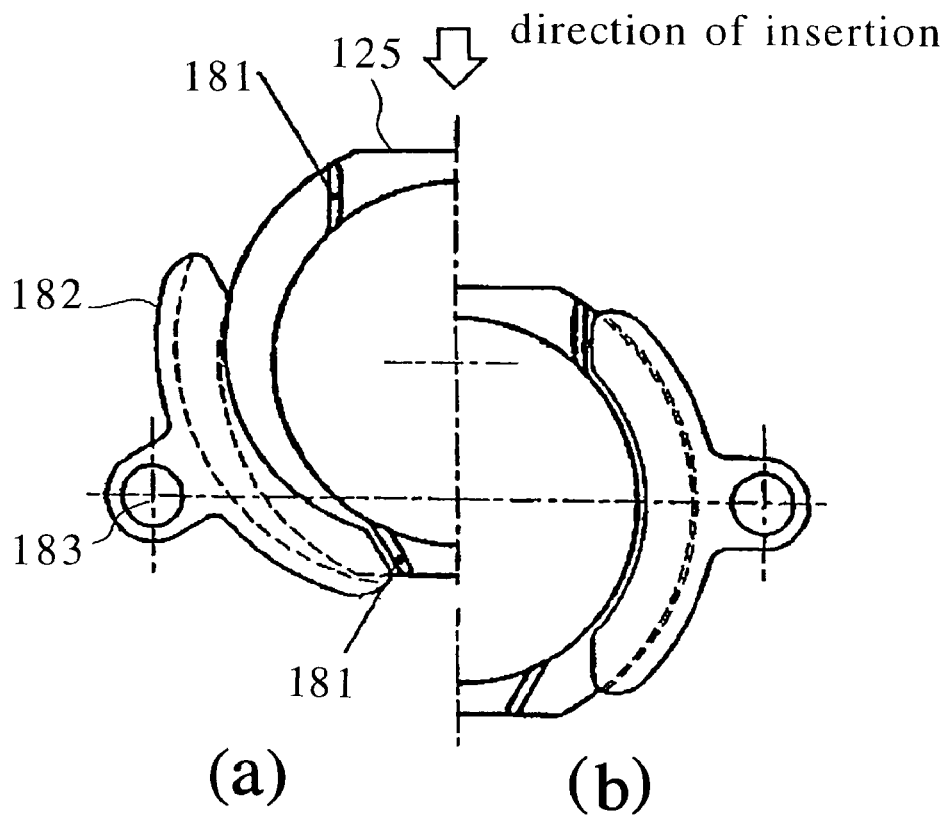
(a)  (b)
direction of insertion
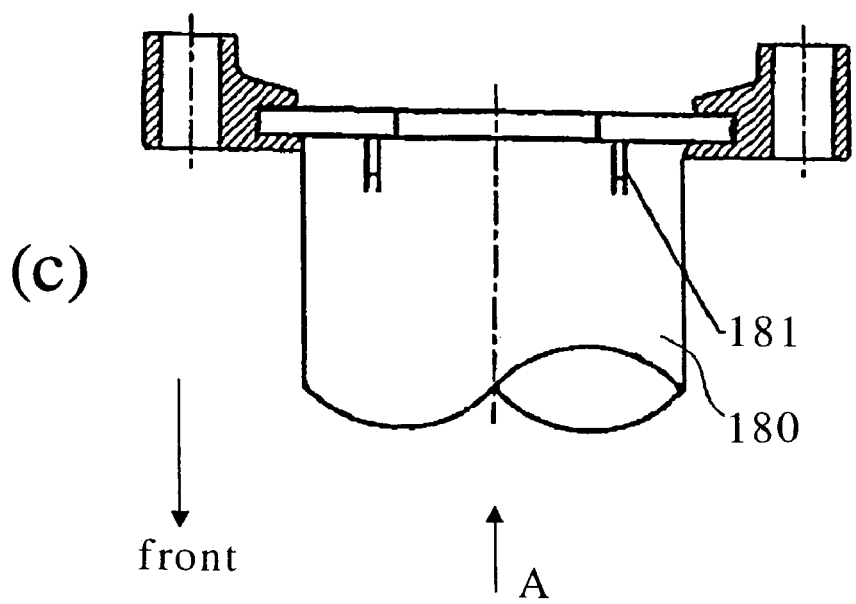
(c)
front   A

FIG.26
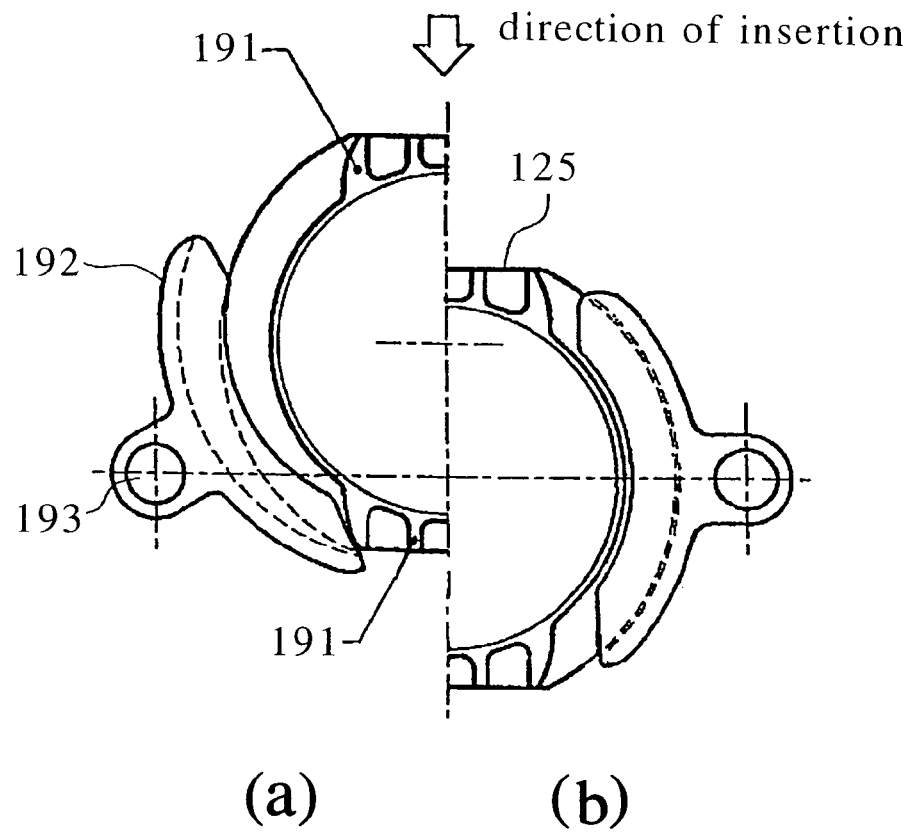
(a)  (b)
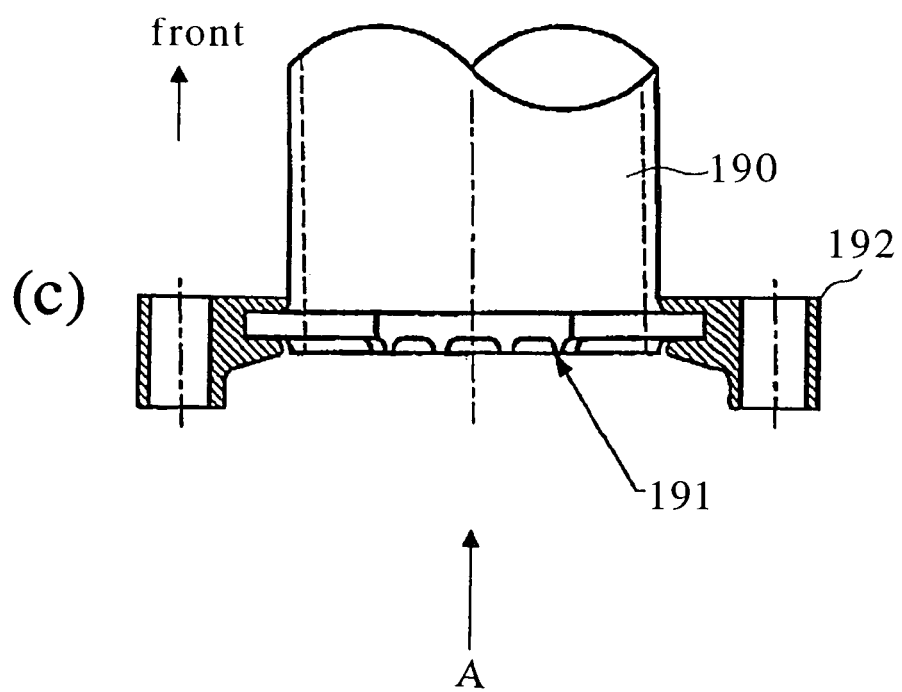
(c)

FIG.29
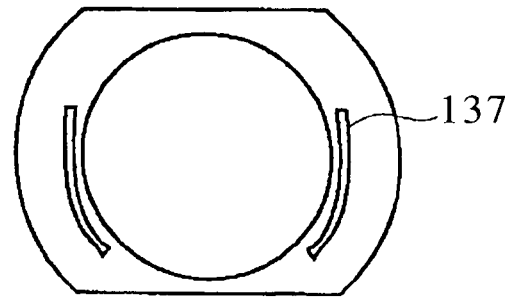
FIG.30
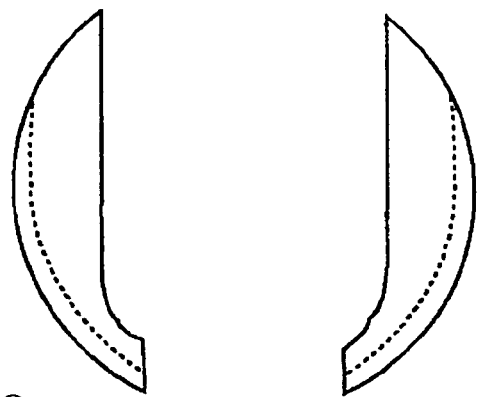
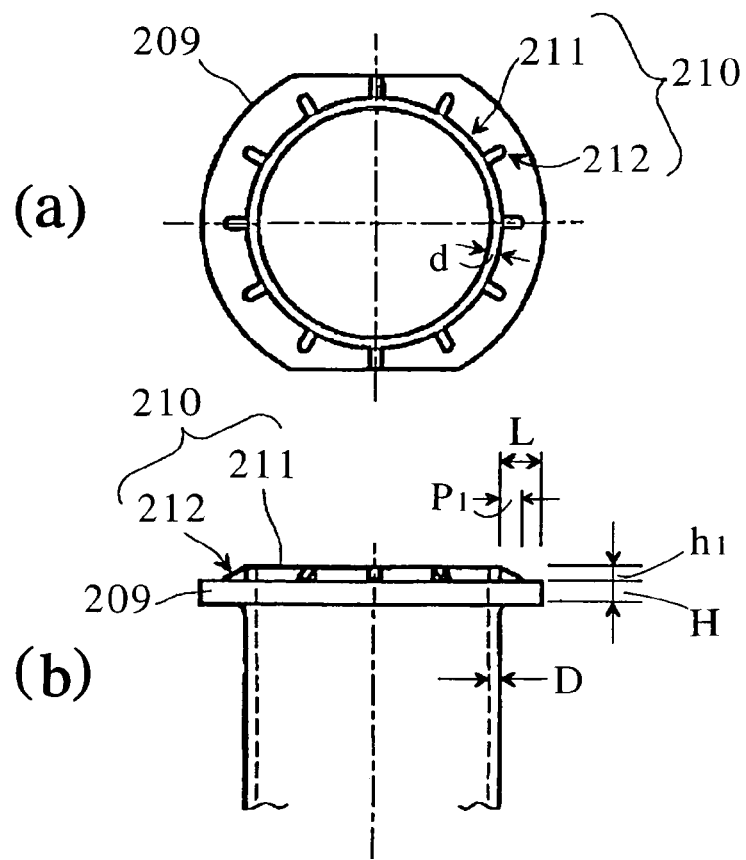

sectional view

SYRINGE BARREL WITH ROUGHENED SURFACE

RELATED APPLICATIONS

This application is a divisional of U.S. patent application Ser. No. 09/780,731, filed Feb. 9, 2001 now U.S. Pat. No. 6,676,635, which claims priority to the following prior foreign applications: Japanese Patent Application No. 2000-033520, filed Feb. 10, 2000; Japanese Patent Application No. 2000-037176, filed Feb. 15, 2000; Japanese Patent Application No. 2000-198358 filed Jun. 30, 2000; and Japanese Patent Application No. 2001-026782 filed Feb. 2, 2001.

BACKGROUND OF THE INVENTION

1. Field of the Invention

The present invention relates to a syringe barrel suitable for injection at high injection pressure using a driving mechanism such as an automatic injector and the like; a cylinder holder used for a syringe driving mechanism such as an automatic injecting apparatus and the like; syringe piston; and piston holder.

2. Description of the Related Art

Syringes are used for injection of liquid in various fields typically including a medical field. Injection of a chemical solution having high viscosity such as a contrast agent for X ray CT imaging and a contrast agent for MRI (magnetic resonance imaging apparatus) requires high pressure, causes difficulty in manual handling, and makes intense jobs. Therefore, it is general to effect injection using a mechanical syringe driving mechanism such as an automatic injection apparatus and the like. FIG. 11 shows a syringe 20 to be mounted on such an automatic injecting apparatus 10. The automatic injecting apparatus 10 comprises a cylinder holder 11, a piston holder 12, and a motor inside (now shown), and the cylinder holder 11 fixes a syringe barrel 21 by holding a flange 22 and the piston holder 12 holds a piston flange 24. A piston 23 can be moved relative to the syringe barrel 21 by progressing or regressing the piston holder 12 by a motor, to effect injection (discharge of liquid from the syringe) or suction of liquid. FIG. 12 shows the syringe 20 mounted on the automatic injecting apparatus 10.

Further, as shown in FIG. 13, when a syringe of smaller size is mounted on this automatic injecting apparatus, the syringe barrel 21 is mounted on a dismountable adaptor 13 (functions as a cylinder holder for the syringe) which is further mounted on the automatic injecting apparatus 10. FIG. 14 shows the syringe 20 mounted on the automatic injecting apparatus 10.

FIG. 16 provides detailed drawings of the adaptor 13 ((a) is a plan view, and (b) is a rear side view)). The syringe barrel 21 can be held by fitting the flange 22 of the syringe barrel 21 into a flange insertion groove 14 of the adaptor 13. For the mounting, as shown in FIG. 15 (a), the flange 22 is fitted into the flange groove 14 while directing a flange cut portion 25 vertically. Then, the flange is rotated by 90° to be fixed so that it is not disconnected. FIG. 15 (b) is a view showing the rotating process, and Fig. (c) is a view showing the use position.

In this constitution, the flange thickness and the flange insertion groove width are so designed to give slight clearance between the flange and flange groove for enabling smooth mounting of the syringe barrel. The reason for this design is also that if the clearance is designed to zero completely, mounting may be sometimes impossible due to certain extent production error to be taken into consideration because the syringe barrel and the cylinder holder (including the adaptor) are usually formed of different materials. Consequently, slight backlash and play in mounted condition is inevitable. However, if there is an error in the mounting procedure, the syringe may sometimes be raised from the right position. If injection of a contrast agent and chemical solution is conducted when fitting in such slight clearance is displaced, the piston shall be pushed under condition in which the flange 22 is inclined relative to the flange insertion groove 14, as shown schematically in FIG. 17, and the total pressure is concentrated only on a part of the flange, and resultantly, in the worst case, the flange may be occasionally broken particularly from the base part.

The cut part of the flange is necessary also for prevention of syringe from rolling down when it is left on a flat surface such as on a table, in addition for such position determination.

Further, the syringe mentioned herein is the enlarged version (100 mL, 200 mL) of a syringe having a generally prevailing form composed of a syringe barrel and a piston. While a generally-used 50 to 60 mL syringe has a pressure resistance of about 3 kg/cm$^2$, the syringe herein shown has an increased pressure resistance of about 20 kg/cm$^2$ to be used for injecting a contrast agent.

On the other hand, there is also a syringe for a contrast agent of no piston type. In this type of syringe, a female screw provided on a member fixing a packing and a male screw on the tip of an axis on the injection apparatus side are connected and the axis is driven back and forth, to suck and inject a contrast agent. However, since such a syringe of no piston type is dedicated to an injector, an automatic injecting apparatus should necessarily used also in sucking a chemical solution. Therefore, during diagnosis, since the automatic injecting apparatus is occupied, sucking of a chemical solution is impossible.

However, a syringe of generally spread type as shown in FIG. 11 and the like has a merit that a chemical solution is filled in the syringe and is prepared previously as a chemical solution for the next inspection, even in diagnosis, since suction of a chemical solution is possible even manually and consequently an automatic injecting apparatus is not necessarily occupied. Further, as shown in FIGS. 11 and 13, there are also a merit that even syringes of different sizes can adopt the same injecting apparatus by using an adaptor, a merit that mounting to an apparatus is easy, and the like.

As described above, there have been made various improvements in syringes for injecting a chemical solution such as a contrast agent and the like, however, when a chemical solution having high viscosity such as a contrast agent is injected, strong force is applied to a flange, consequently, the syringe may occasionally be broken if there are a small number of flange surfaces receiving pressure. If the flange is not rotated to given position and if injection is conducted, for example, in halfway condition as shown in FIG. 15 (b), crisis of breakage increases due to small area receiving pressure.

Further, in an apparatus for injection using a relatively large syringe having a size of about 200 mL, there has been recently contrived a mechanism for clamping in which a cylinder holder portion is mobilized and mounting of a flange can be effected simply and securely. FIG. 18 is an enlarged view of a cylinder holder portion of such an automatic injecting apparatus 110. This cylinder holder has two clamps 116, and before mounting of a syringe, the upper part of two clamps are open as shown in FIG. 18. Then, in FIG. 19 (a) (upper left view in FIG. 19), the syringe is fitted in two clamps 116 in open state while directing the flange cut surface vertically. With progress of fitting, two clamps 116 are pushed by the flange 122 and rotated around the fulcrum 117, leading to closed condition. By rotating the flange by 90°, the syringe is fixed while the flange cut surfaces 125 being situated at upper and lower positions as shown in FIG. 19 (b) (upper right view in FIG. 19). FIG. 19 (c) is a plan view of the fixed condition watched from the upper side (clamp part is drawn in sectional view).

However, even if such a clamp mechanism is used, when a syringe is fixed at a halfway position in a process from Fig. (a) to Fig. (b), the pressure-receiving area of the flange decreases in injection and crisis of syringe breakage increases like the above-mentioned case.

SUMMARY OF THE INVENTION

A purpose of the present invention is to prevent breakage of a syringe barrel in injecting liquid of high viscosity at high pressure. For this purpose, an objective of one aspect of the present invention is to provide an improved syringe barrel which is not easily broken. Further, an objective of another aspect of the present invention is to provide a cylinder holder which causes no breakage of a syringe even if the syringe used is of usual type. Still further, an objective of another aspect of the present invention is to provide a cylinder holder which is used together with an improved syringe barrel and causes no breakage of a syringe.

The aspects of the present invention is as follows.

A syringe barrel, comprising a flange where at least one of the front surface and the rear surface of the flange is roughened.

The syringe barrel according to above aspect, wherein the front surface of the flange is roughened.

The above-mentioned syringe barrel can be combined with a syringe piston and used in a pre-filled syringe filled with a chemical solution. As this chemical solution, a contrast agent is exemplified.

In the present invention, the term "cylinder holder" means one which can hold a syringe barrel by a groove, and when a syringe barrel is mounted on an adaptor before being set in an injecting apparatus, the term "cylinder holder" is construed to include such adaptor. The cylinder holder is usually incorporated in an automatic injecting apparatus, or integrated with an automatic injecting apparatus as one body.

As an automatic injecting apparatus to which the present invention is applied, the apparatus as shown in FIGS. 11, 13 and 18 is typically exemplified. This automatic injecting apparatus 10 can be used together with a controller 15 (operation mechanism) including a display, keyboard and the like as shown, for example, in FIG. 41. Alternatively, as shown in FIG. 42, it can be applied to an automatic injecting apparatus obtained by integrating a piston driving mechanism 16 with an operation mechanism 17 including a display, keyboard and the like. In this automatic injecting apparatus, the syringe barrel 21 can be held by the cylinder holder 18.

(a) is a view showing fitting of a flange with a flange insertion groove of a cylinder holder.

(b) is an enlarged view of a flange insertion groove of a cylinder holder.

(c) is an enlarged view of a flange.

FIG. 3(a) is a view showing a syringe barrel of Embodiment A-1. FIG. 3(b) is an enlarged view of the B-part; FIG. 3(c) is an x-x sectional view; FIG. 3(d) is a y-y sectional view.

FIGS. 4(a)-(c) are views of the syringe barrel of Embodiment A-2. FIG. 4(a) is a rear sideview; FIG. 4(b) is an enlarged view of the C part; FIG. 4(c) is an x-x sectional view.

FIGS. 5(a)-(d) are views of the syringe barrel of Embodiment A-3. FIG. 5(a) is a rear side view; FIG. 5(b) is an enlarged view of the D part; FIG. 5(c) is an x-x sectional view; FIG. 5(d) is a y-y sectional view.

FIGS. 6(a)-(b) are views showing an example of a cylinder holder having a concave portion. FIG. 6(a) is the cylinder holder and FIG. 6(b) is the cylinder holder with the syringe barrel mounted.

Figure 7:
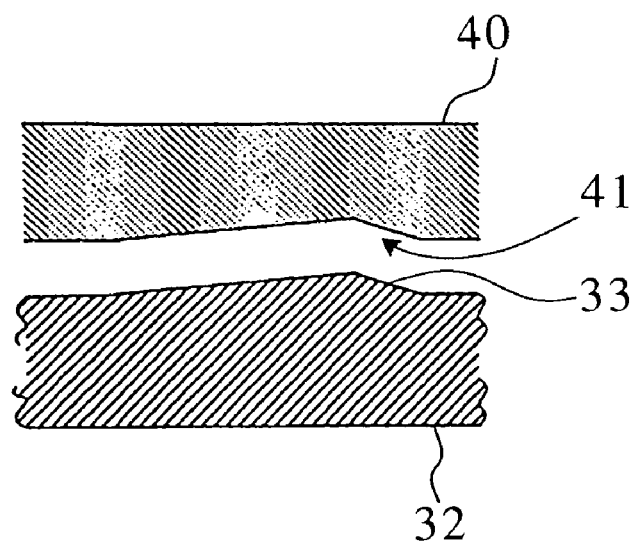

FIG. 7 is a view showing one example of a concave form (sectional view along vertical direction to paper surface in FIG. 6 (b)).

Figure 8:
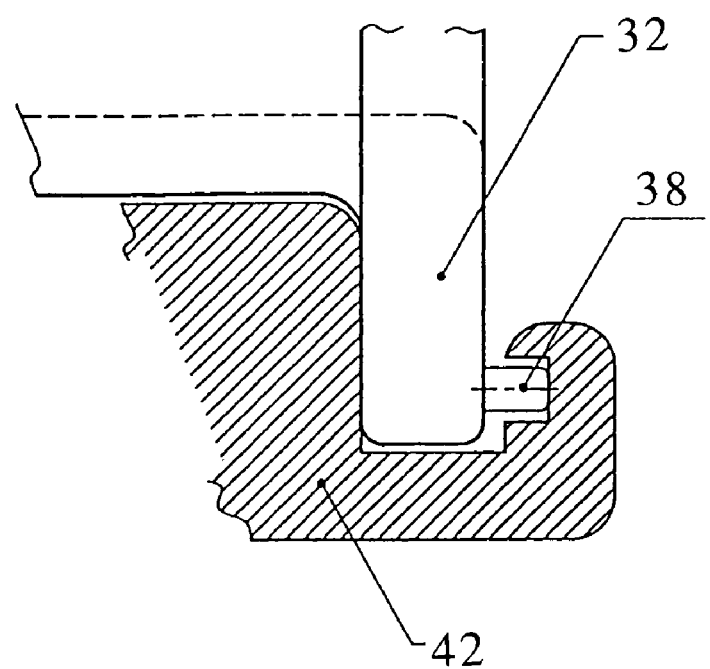

FIG. 8 is a view showing another form of a cylinder holder having a concave portion.

Figure 9:
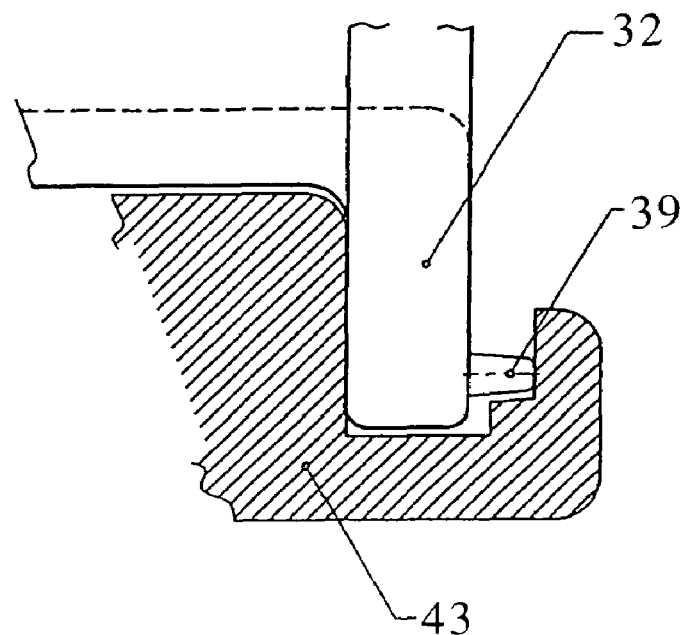

FIG. 9 is a view showing another form of a cylinder holder having a concave portion.

Figure 10:
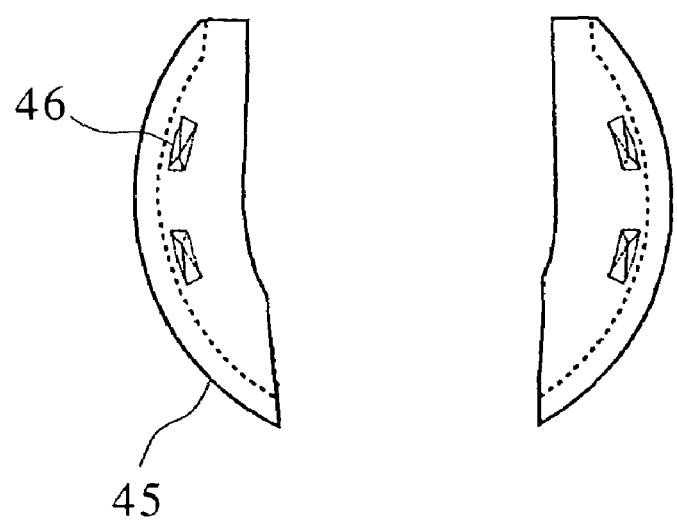

FIG. 10 is a view showing one example of a cylinder holder having a projection provided on the inner surface of a flange insertion groove.

Figure 11:
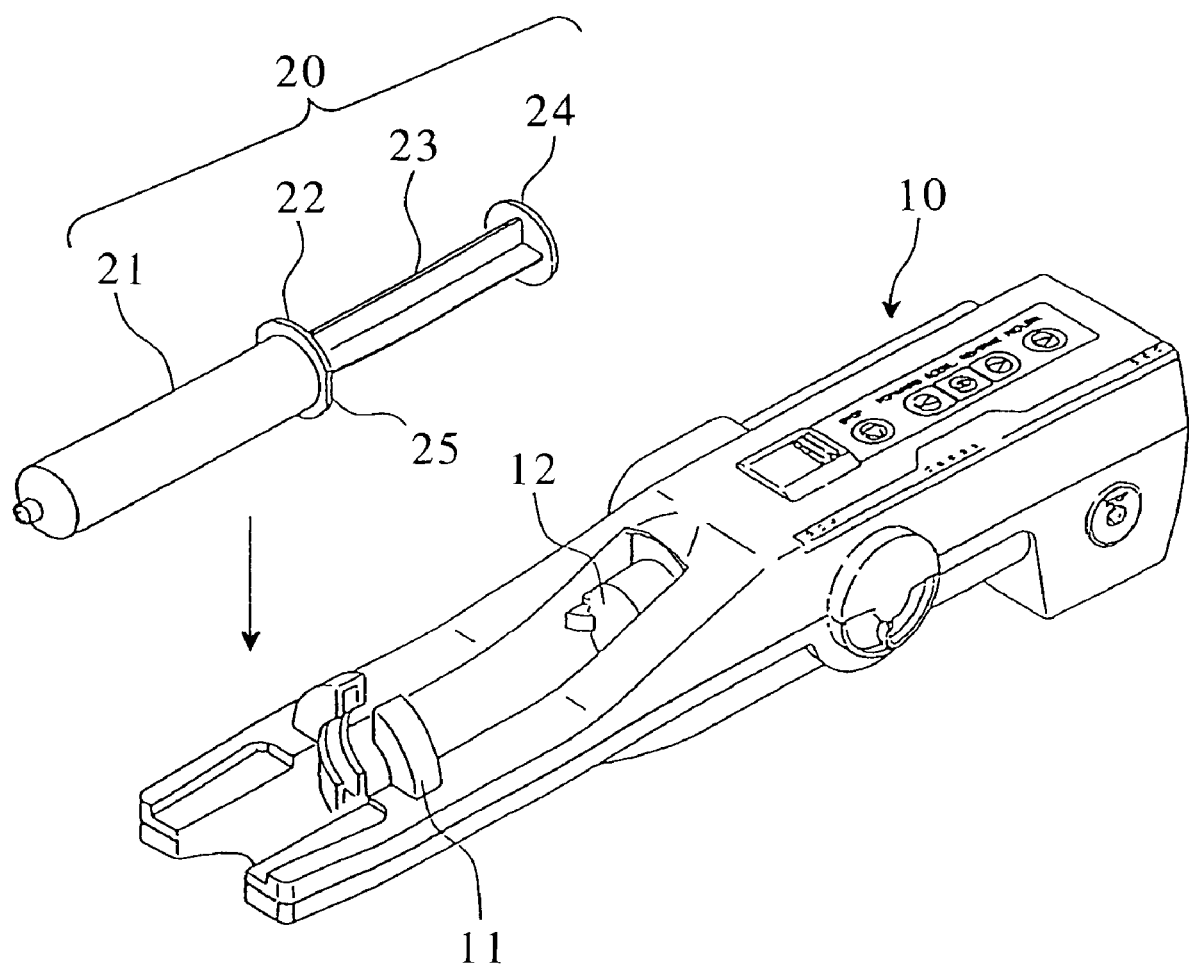

FIG. 11 is a view showing a syringe to be mounted on an automatic injecting apparatus.

Figure 12:
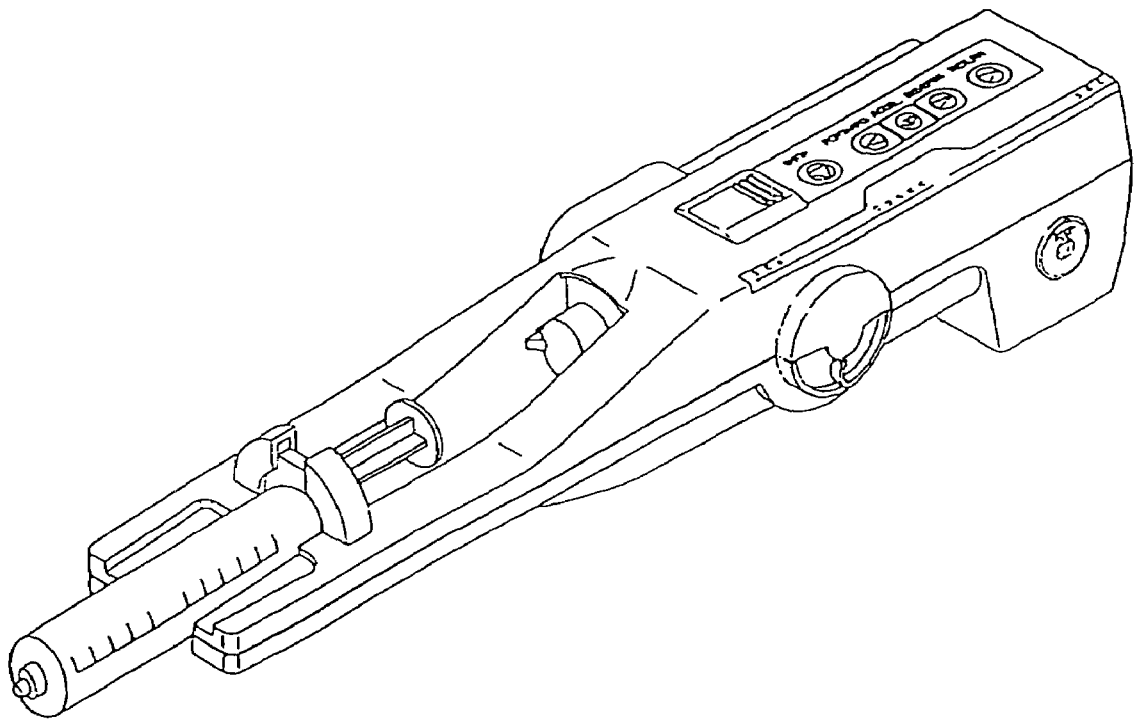

FIG. 12 is a view showing a syringe mounted on an automatic injecting apparatus.

Figure 13:
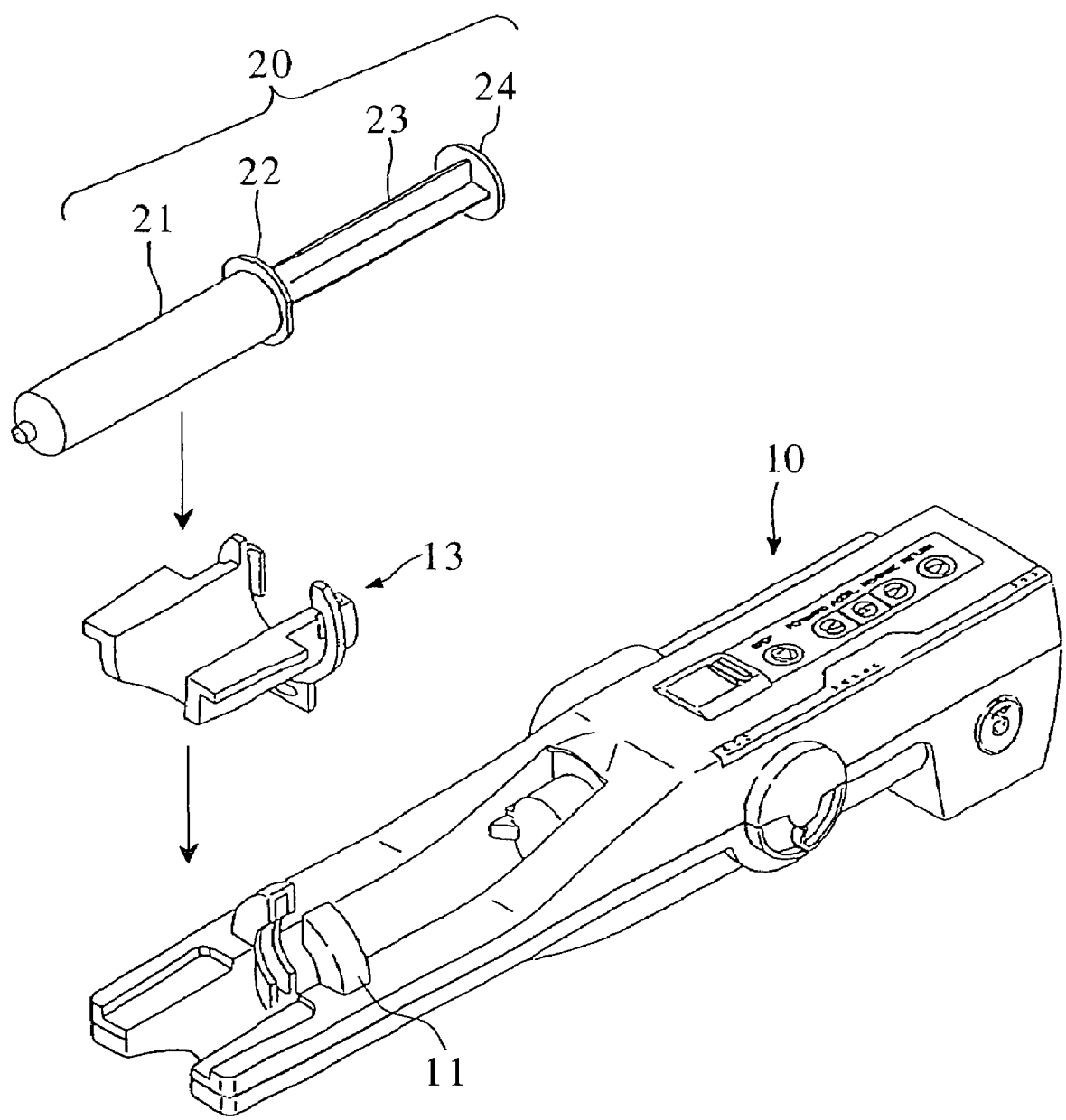

FIG. 13 is a view showing a syringe to be mounted on an automatic injecting apparatus by using an adaptor.

Figure 14:
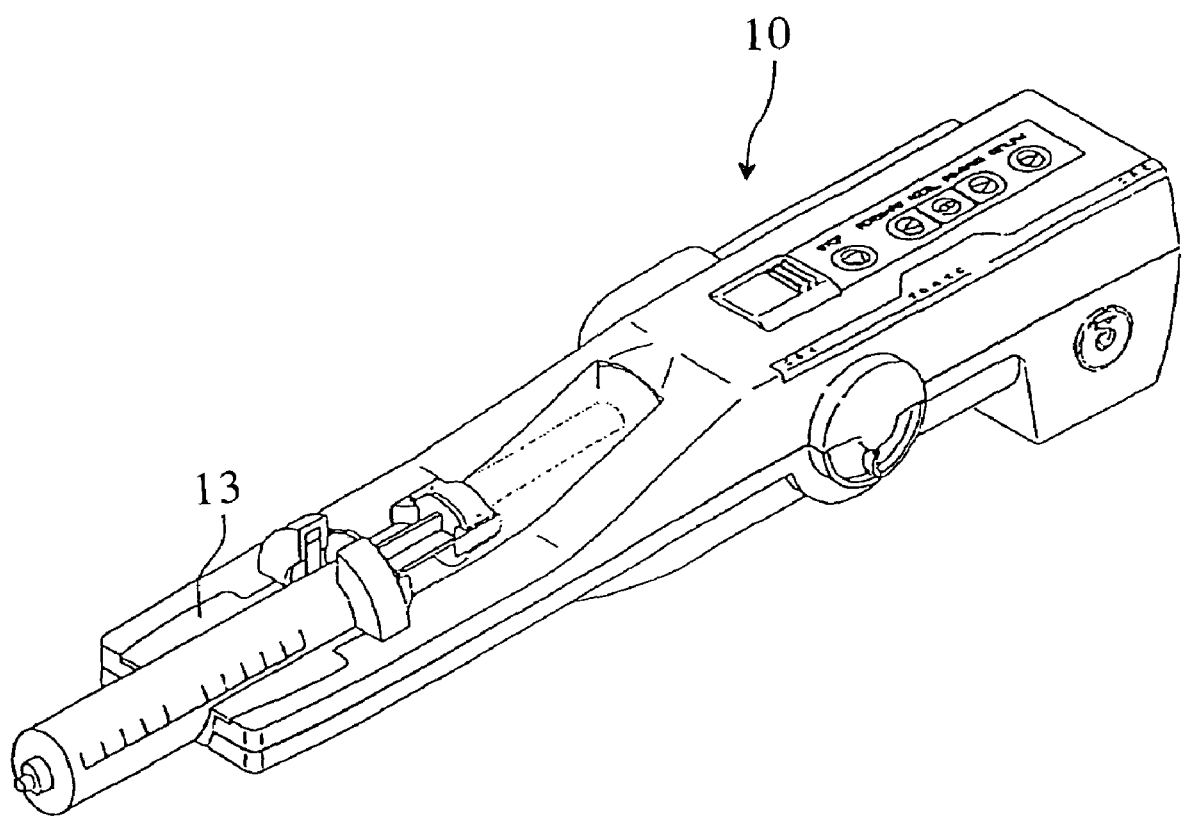

FIG. 14 is a view showing a syringe mounted on an automatic injecting apparatus.

FIGS. 15(a)-(c) are views illustrating holding and positioning of a syringe by a cylinder holder (adaptor) of an automatic injecting apparatus shown in FIGS. 11 and 13. FIG. 15(a) is a plan view of the mounting of the syringe; FIG. 15(b) is a rear side view; and FIG. 15(c) is a view showing the use position.

Figure 16:
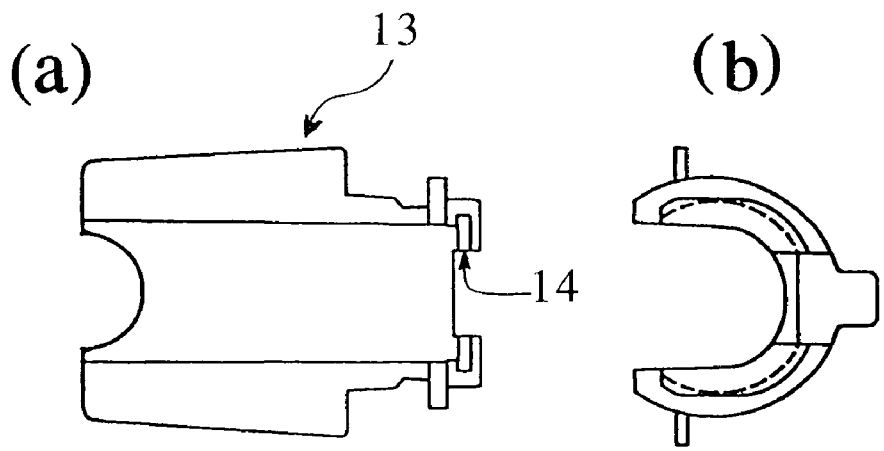

FIG. 16(a)-(b) are enlarged views of an adaptor. FIG. 16(a) is a plan view and FIG. 16(b) is a rear side view.

Figure 17:
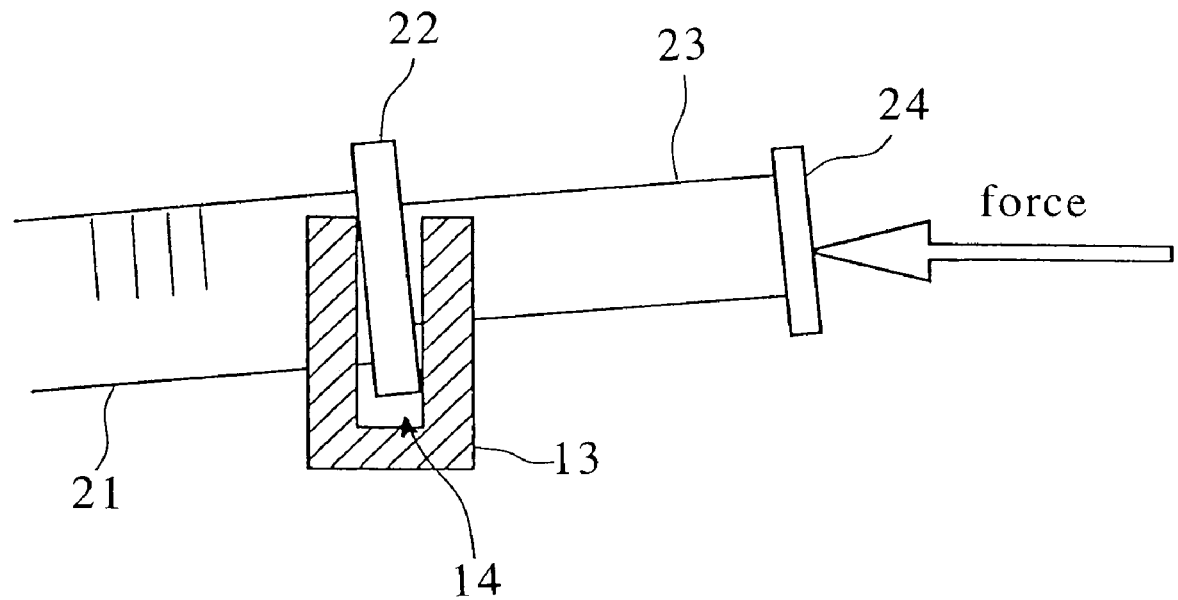

FIG. 17 is a schematic view of a flange of a syringe barrel, which is raised from right position and displaced from a cylinder holder.

Figure 18:
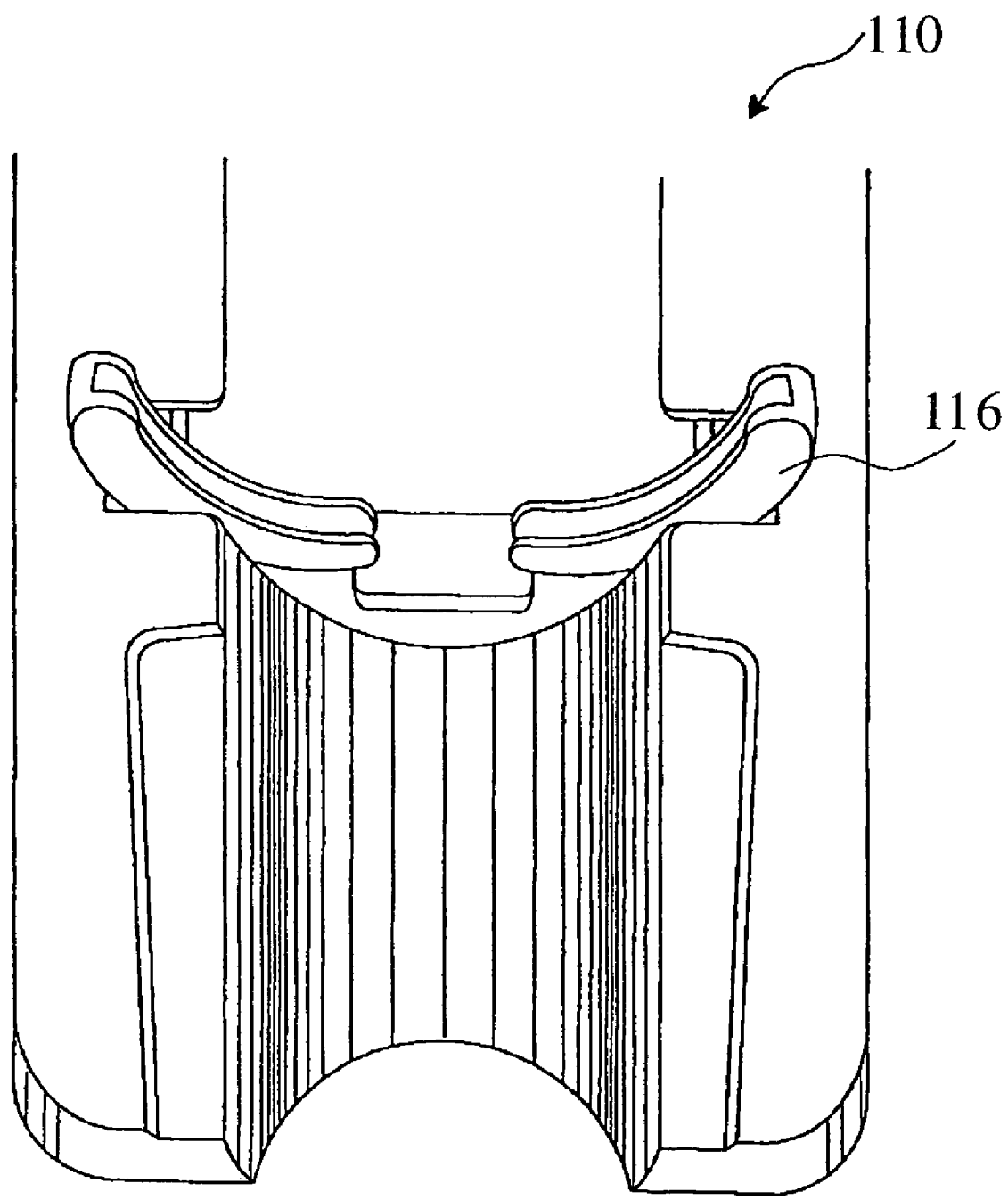

FIG. 18 is a view showing a cylinder holder equipped with two movable clamps.

FIG. 19 is a view illustrating holding and positioning of a syringe by a cylinder holder equipped with two movable clamps.

(a) is a view showing mounting of a syringe watched from the rear side of the syringe.

(b) is a view showing a syringe after mounting watched from the rear side of the syringe.

(c) is a top view showing a syringe after mounting.

Figure 20:
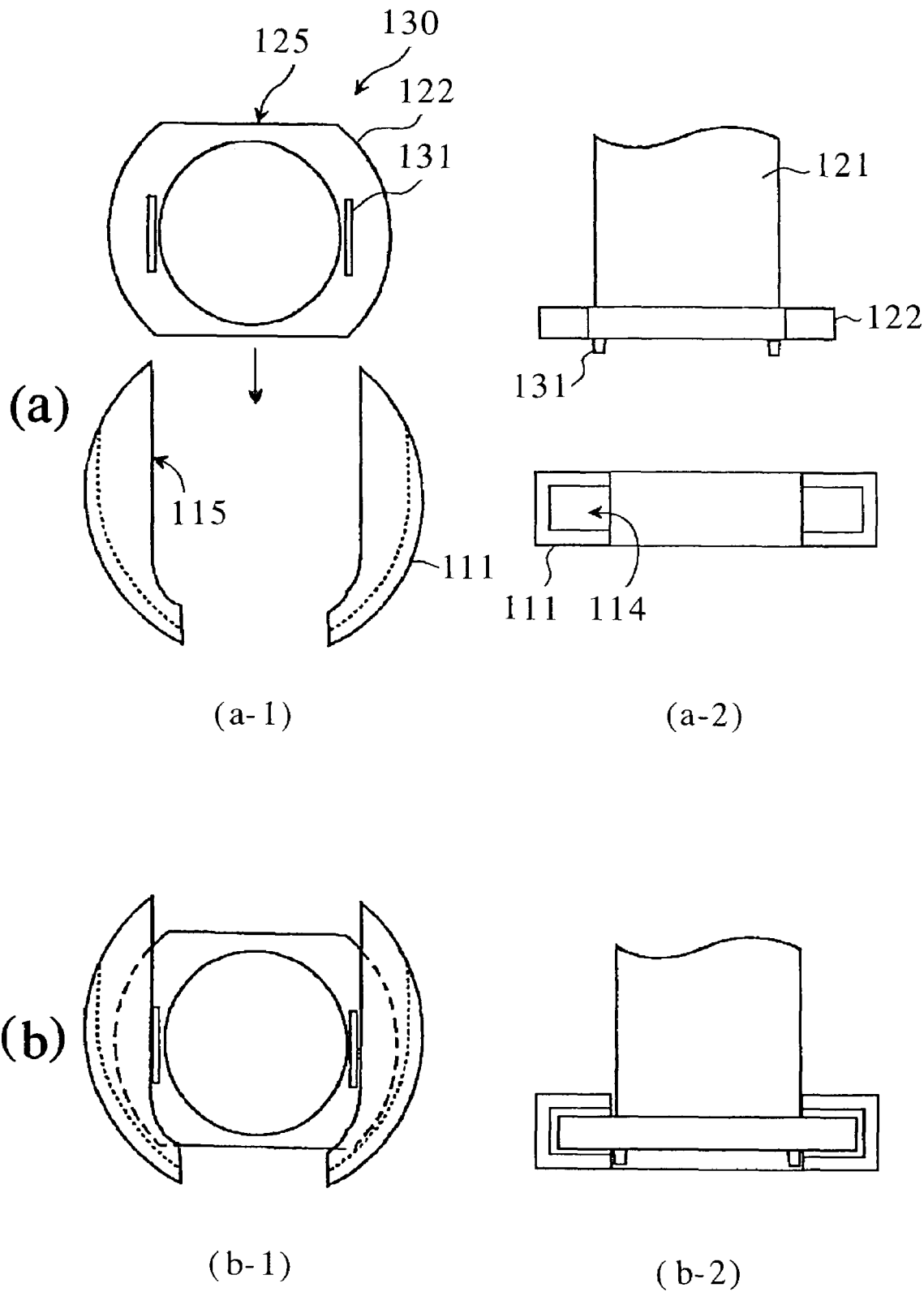

FIG. 20 is a view showing one embodiment of a syringe of the present invention, and a cylinder held and fixed by a cylinder holder.

(a-1) is a view showing state before syringe mounting watched from the rear side of the syringe.

(a-2) is a top view of a syringe and cylinder holder.

(b-1) is a view showing state before syringe mounting watched from the rear side of the syringe.

(b-2) is a top view after syringe mounting.

Figure 21:
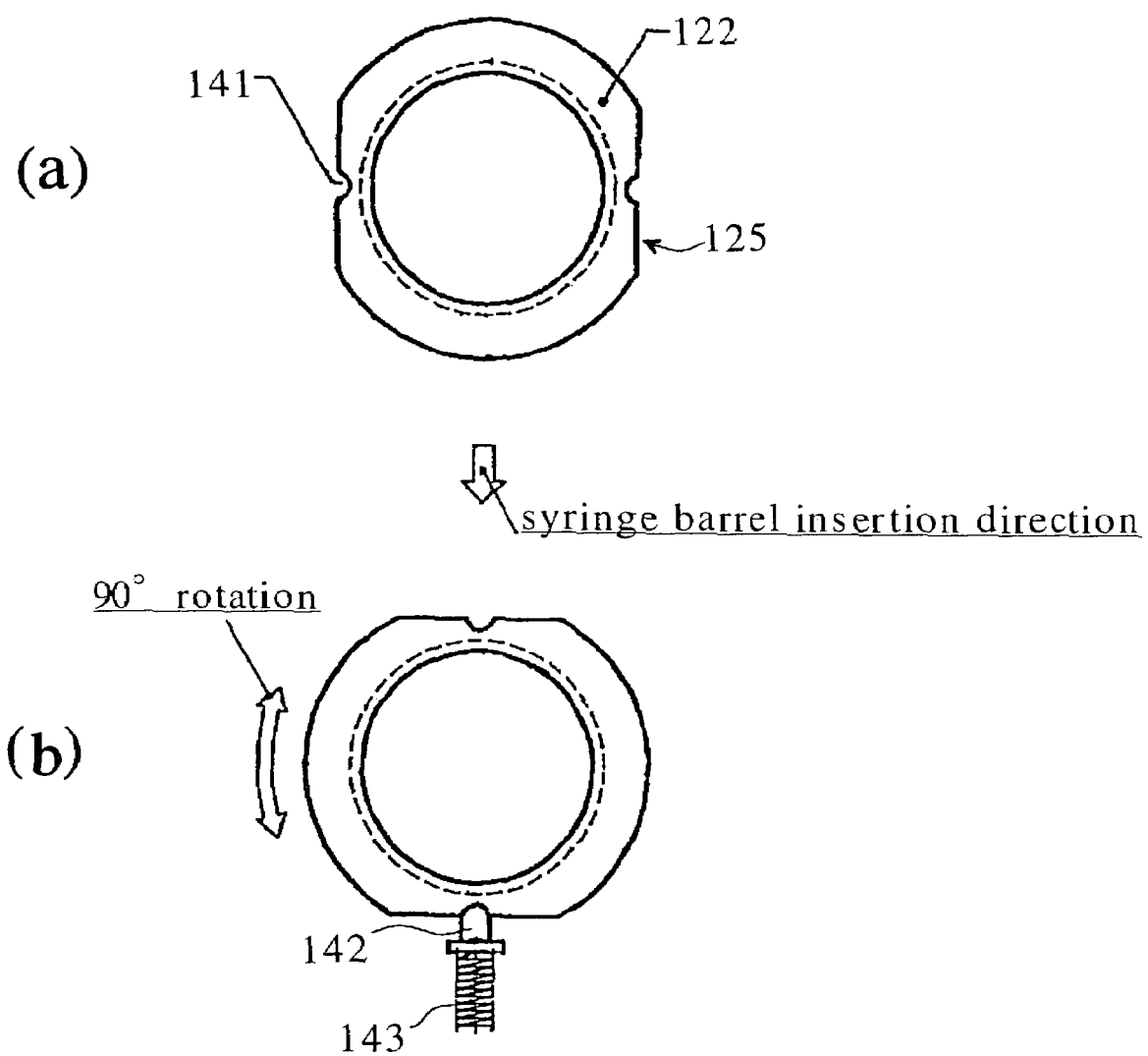

FIG. 21 is a view showing one embodiment of a syringe and cylinder holder of the present invention.

(a) is a view showing state before syringe mounting watched from the rear side of the syringe.

(b) is a view showing state after syringe mounting watched from the rear side of the syringe.

Figure 22:
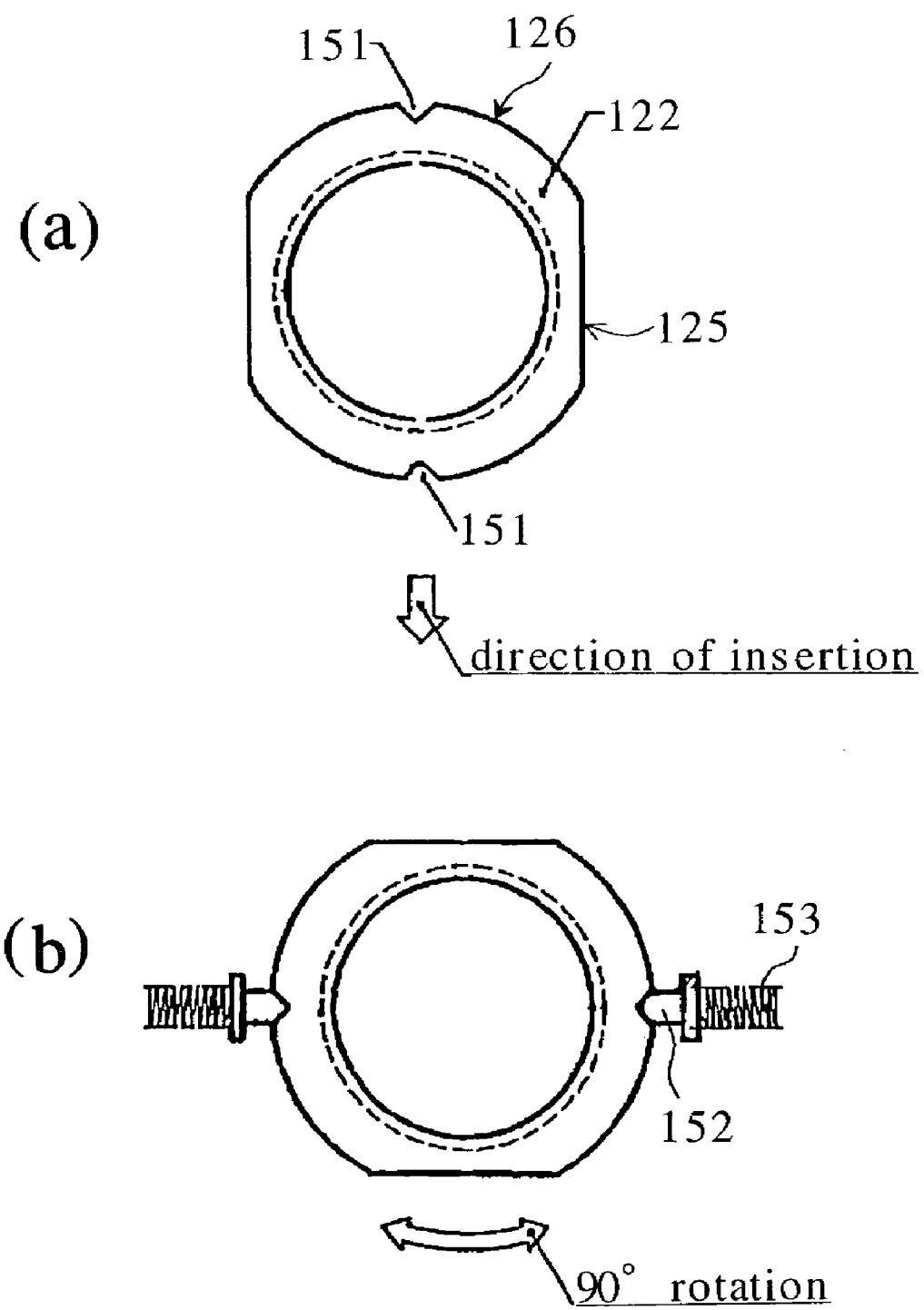

FIG. 22 is a view showing one embodiment of a syringe and cylinder holder of the present invention.

(a) is a view showing state before syringe mounting watched from the rear side of the syringe.

(b) is a view showing state after syringe mounting watched from the rear side of the syringe.

Figure 23:
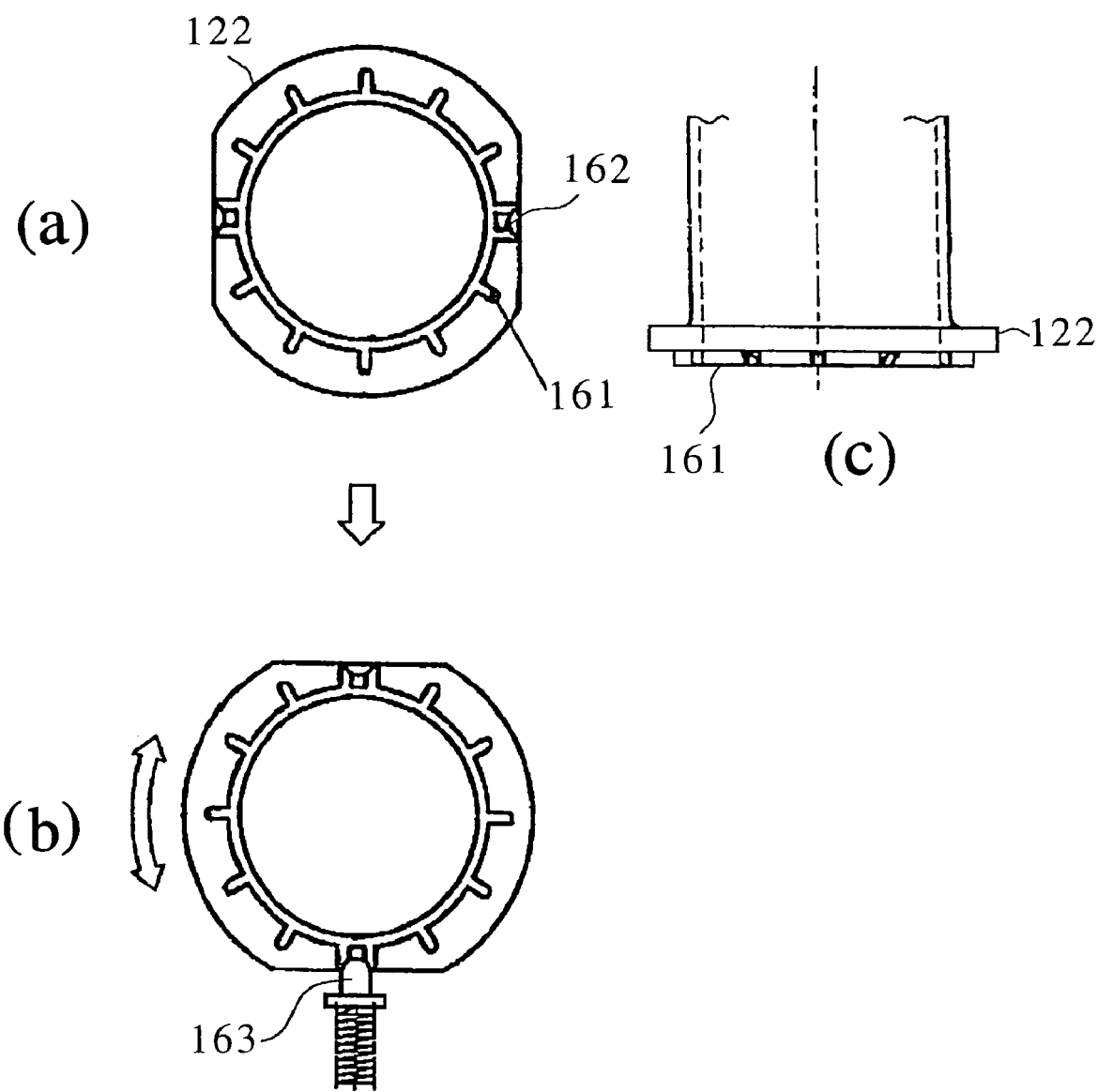

FIG. 23 is a view showing one embodiment of a syringe and cylinder holder of the present invention.

(a) is a view showing state before syringe mounting watched from the rear side of the syringe.

(b) is a view showing state after syringe mounting watched from the rear side of the syringe.

(c) is a top view of a syringe.

Figure 24:
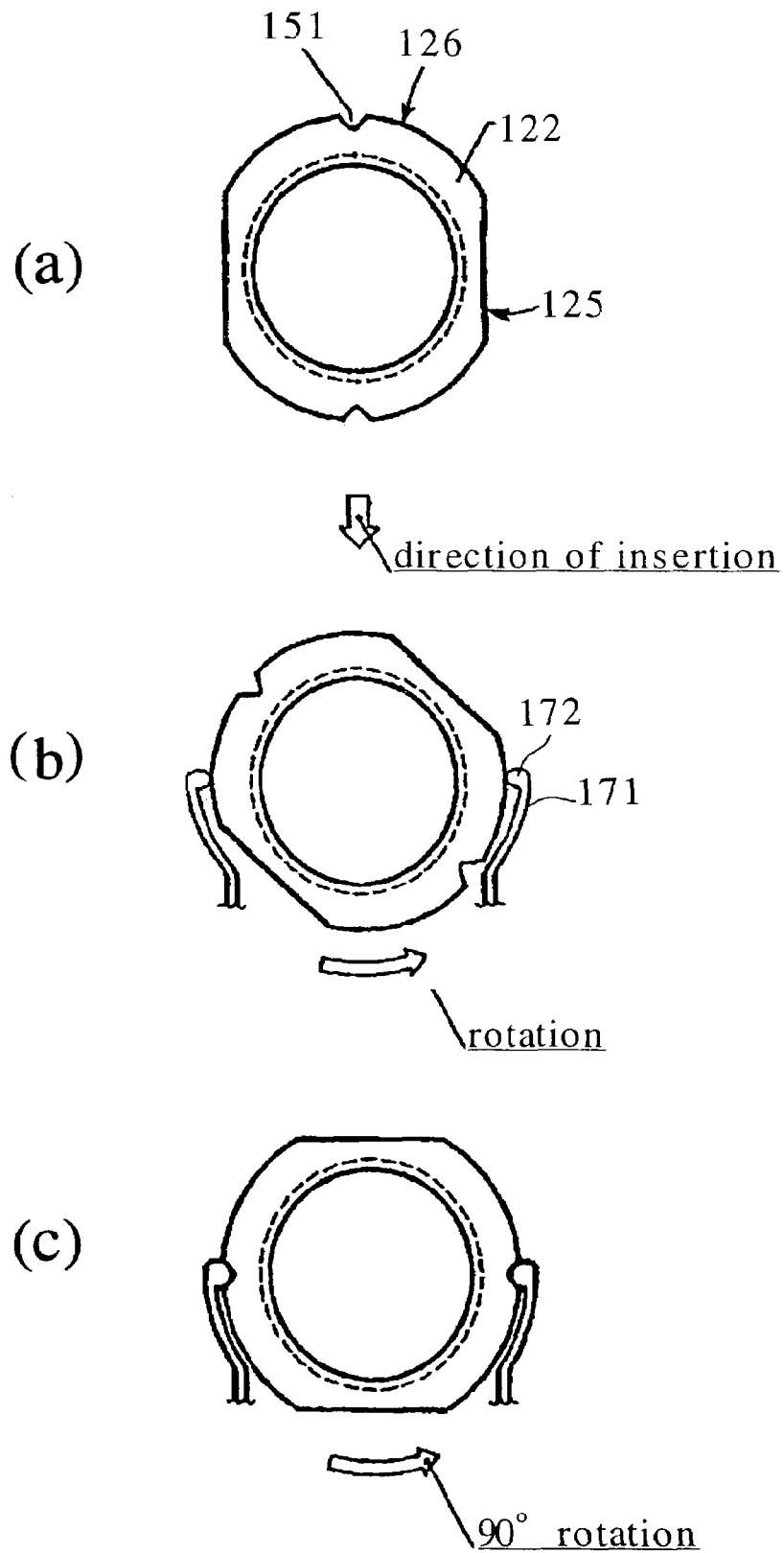

FIG. 24 is a view showing one embodiment of a syringe and cylinder holder of the present invention.

(a) is a view showing state before syringe mounting watched from the rear side of the syringe.

(b) is a view showing state in the process of syringe mounting watched from the rear side of the syringe.

(c) is a view showing state after syringe mounting watched from the rear side of the syringe.

FIG. 25 is a view showing one embodiment of a syringe of the present invention, and a cylinder held and fixed by a cylinder holder.

(a) is a view showing syringe mounting watched from the front side of the syringe.

(b) is a view showing state after syringe mounting watched from the front side of the syringe.

(c) is a top view showing state after syringe mounting.

FIG. 26 is a view showing one embodiment of a syringe of the present invention, and a cylinder held and fixed by a cylinder holder.

(a) is a view showing syringe mounting watched from the front side of the syringe.

(b) is a view showing state after syringe mounting watched from the rear side of the syringe.

(c) is a top view showing state after syringe mounting.

Figure 27:
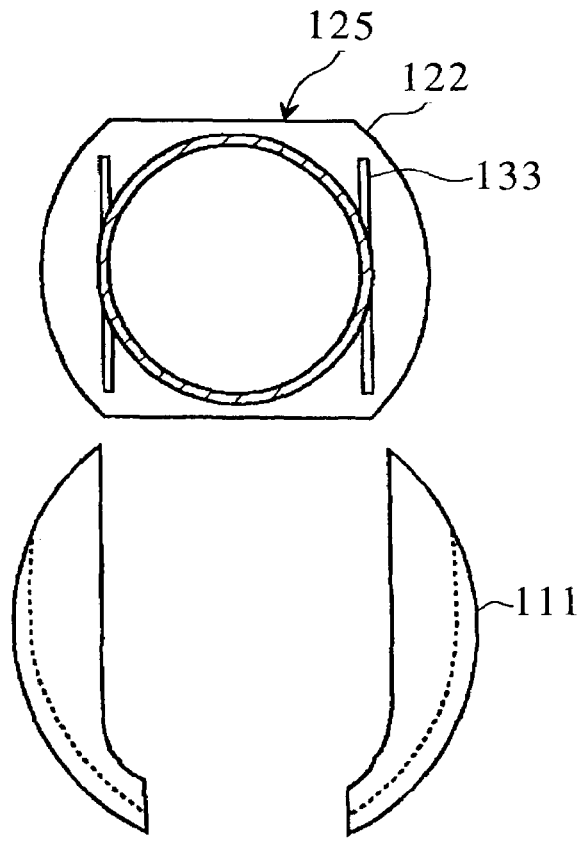

FIG. 27 is a view showing one embodiment of a syringe of the present invention.

Figure 28:
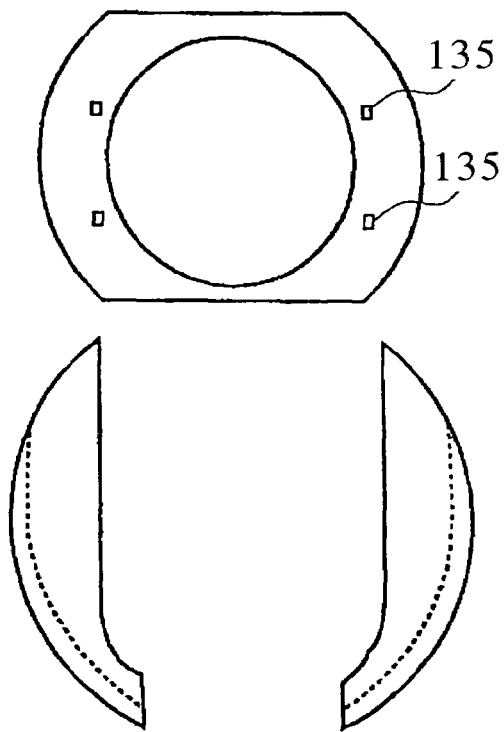

FIG. 28 is a view showing one embodiment of a syringe of the present invention.

FIG. 29 is a view showing one embodiment of a syringe of the present invention.

FIG. 30 is a view showing one example of a syringe barrel of the present invention.

(a) is a side view (watched from the rear side).

(b) is a side view (watched from the lateral side).

Figure 31:
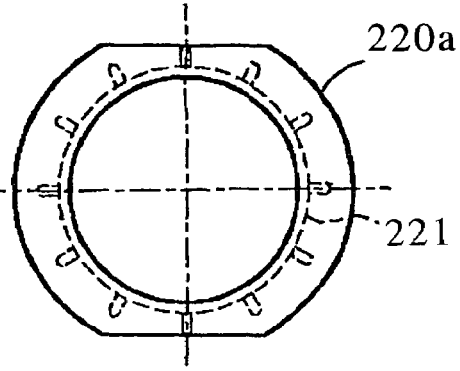

FIG. 31 is a view showing one example of a syringe barrel of the present invention.

(a) is a side view (watched from the rear side).

(b) is a side view (watched from the lateral side).

Figure 32:
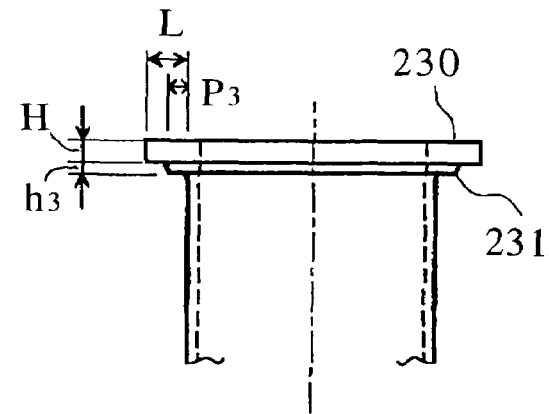

FIG. 32 is a view showing one example of a syringe barrel of the present invention.

(a) is a side view (watched from the rear side).

(b) is a side view (watched from the lateral side).

Figure 33:
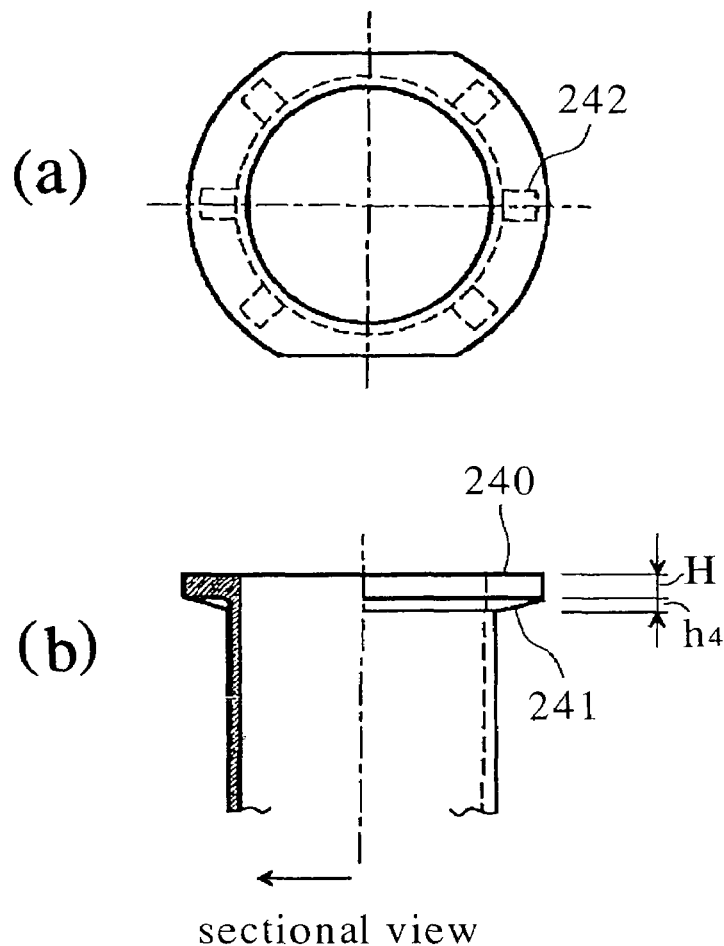

FIG. 33 is a view showing one example of a syringe barrel of the present invention.

(a) is a side view (watched from the rear side).

(b) is a side view (watched from the lateral side).

Figure 34:
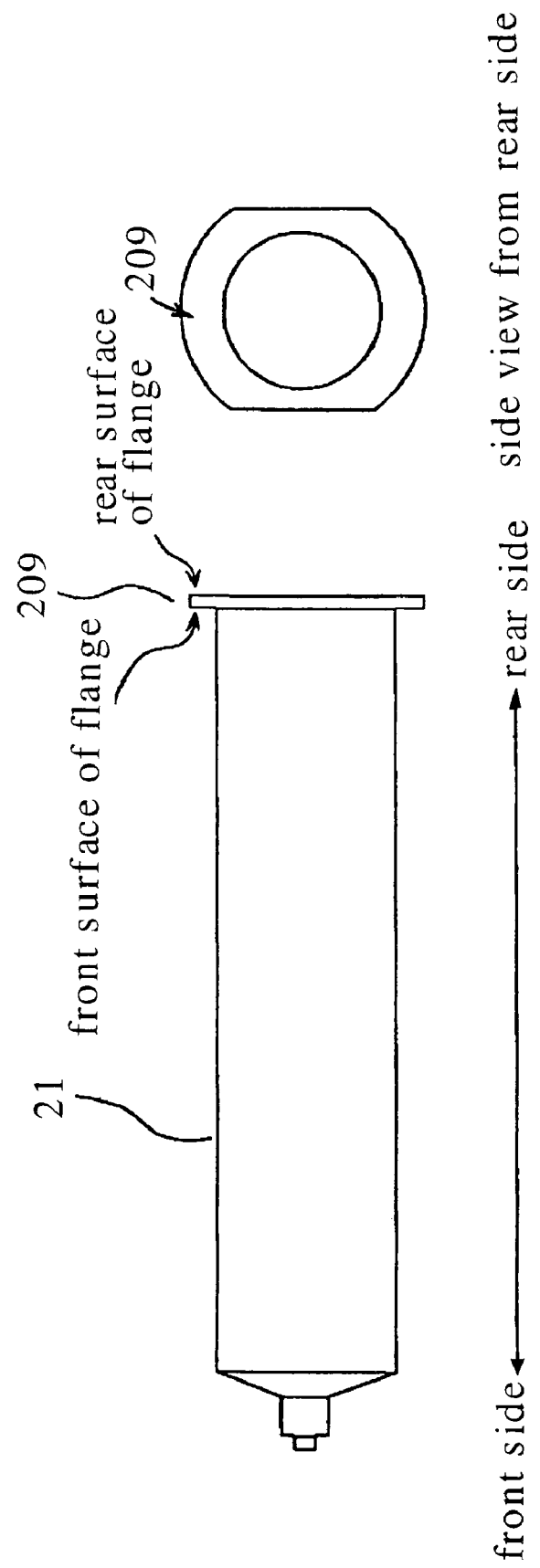

FIG. 34 is a view showing a generally-used syringe barrel.

Figure 35:
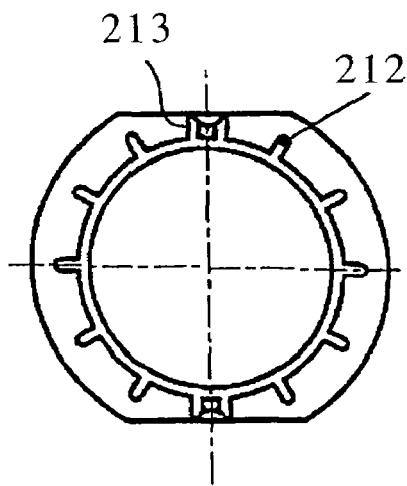

FIG. 35 is a view showing another one example of a reinforcing rib.

Figure 36:
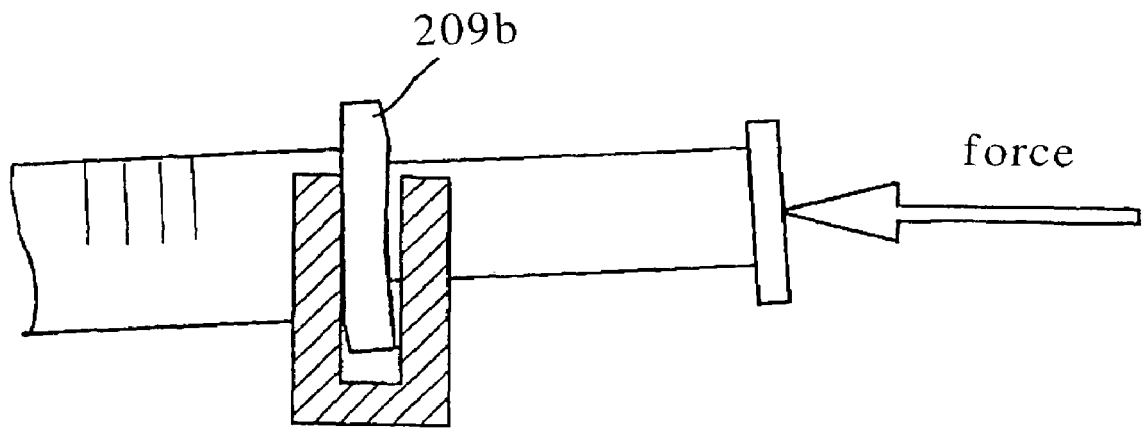

FIG. 36 is a view schematically showing a syringe barrel (having distortion in flange) held by a groove.

Figure 37:
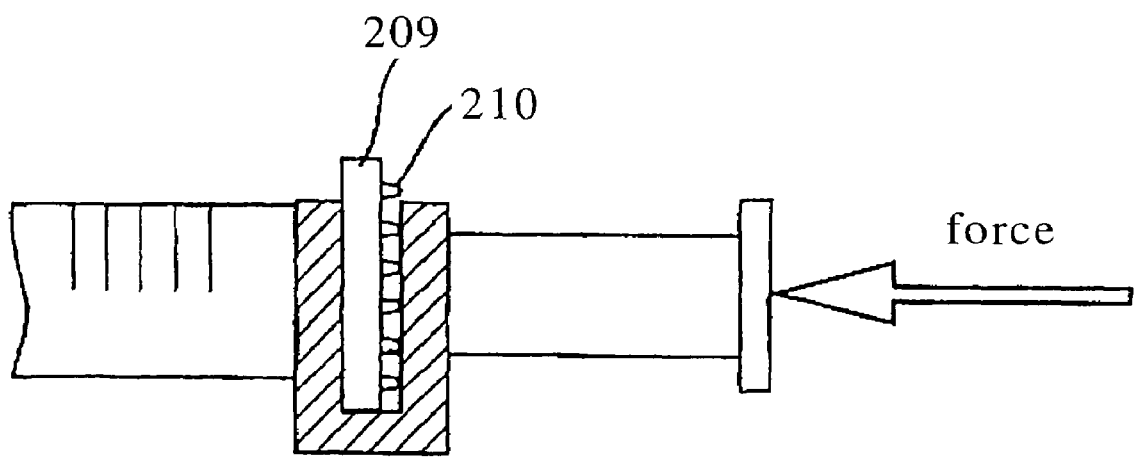

FIG. 37 is a view schematically showing a syringe barrel (reinforcing rib is provided on the rear surface of a flange) held by a groove.

FIG. 38(a)-(c) are views showing one example of a syringe barrel. FIG. 38(a) is a section of the syringe barrel; FIG. 38(b) is a side view from the B direction; and FIG. 38(c) is a side view from the C direction.

Figure 39:
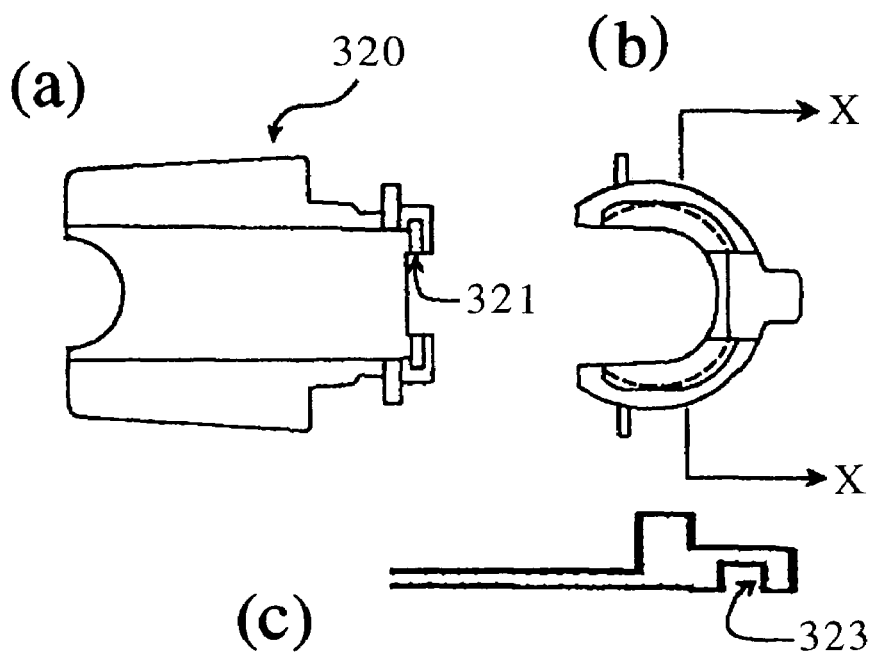

FIGS. 39(a)-(c) are views showing one example of a cylinder holder (adaptor). FIG. 39(a) is a top view; FIG. 39(b) is a side view; and FIG. 39 (c) is an enlarged view of an x-x section.

Figure 40:
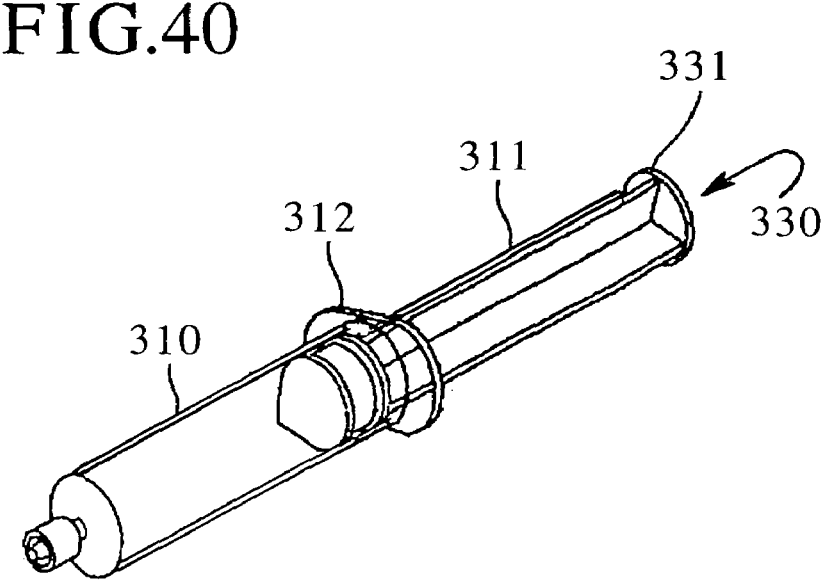

FIG. 40 is a view showing a syringe where a piston is drawn out.

Figure 41:
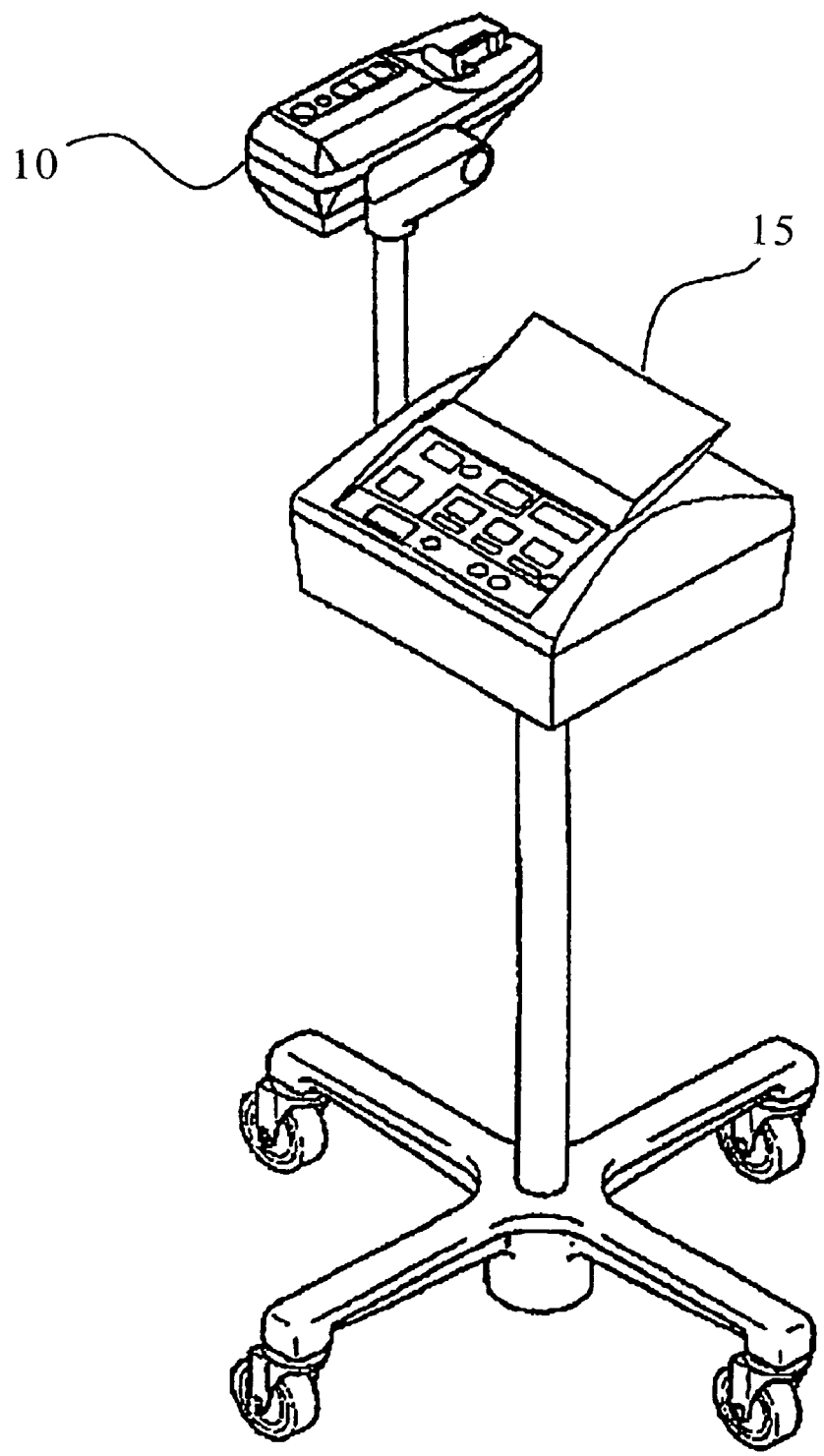

FIG. 41 is a view showing one example of an automatic injecting apparatus in which a piston driving mechanism and an operation mechanism are made separately as different bodies.

Figure 42:
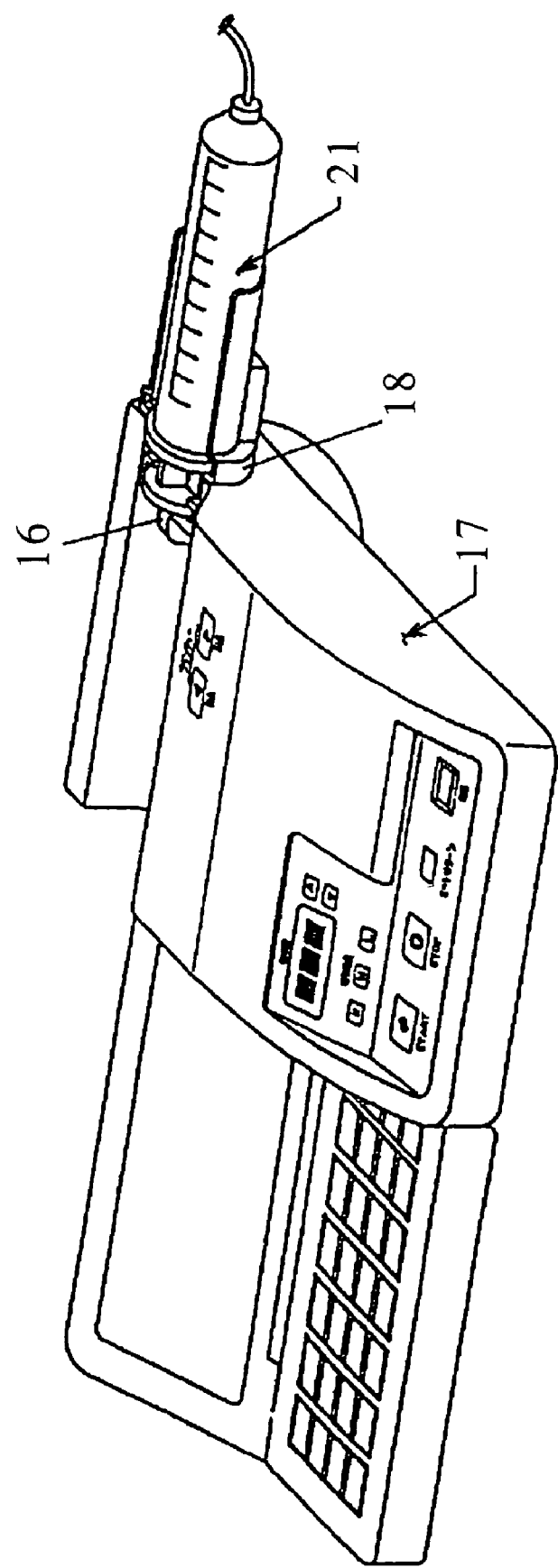

FIG. 42 is a view showing one example of an automatic injecting apparatus in which a piston driving mechanism and an operation mechanism are integrated.

DETAILED DESCRIPTION OF THE PREFERRED EMBODIMENT

The embodiments of the present invention will be illustrated by four divided sections.

Part I

In this part, description will be made for a syringe barrel and/or cylinder holder where a projection is equipped so as to fix the flange of the syringe barrel in the flange insertion groove provided on the cylinder holder.

Embodiment of Syringe Barrel Having Projection

Figure 1:
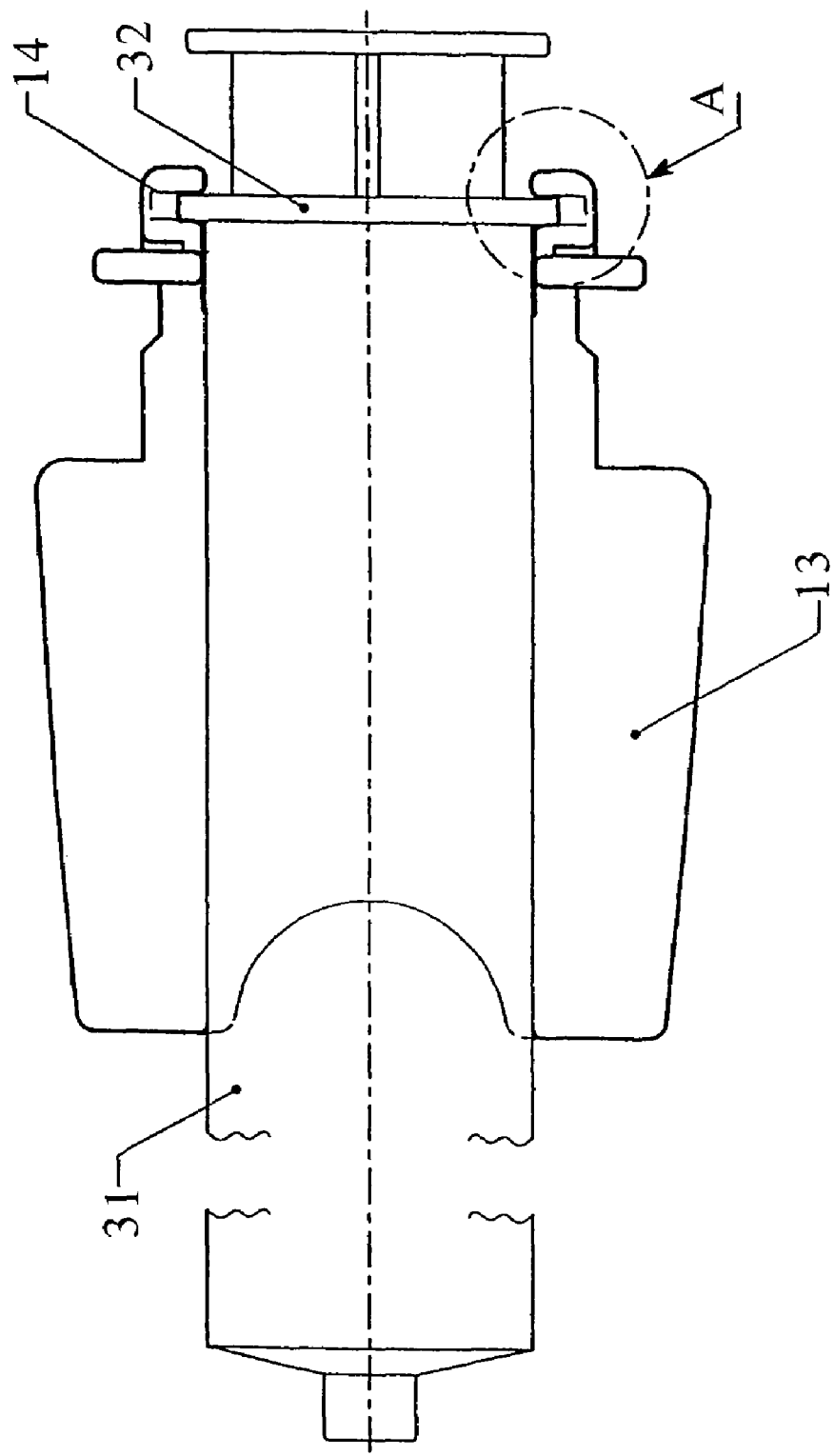
FIG. 1 is a view showing a syringe barrel mounted on a cylinder holder.
Figure 2:
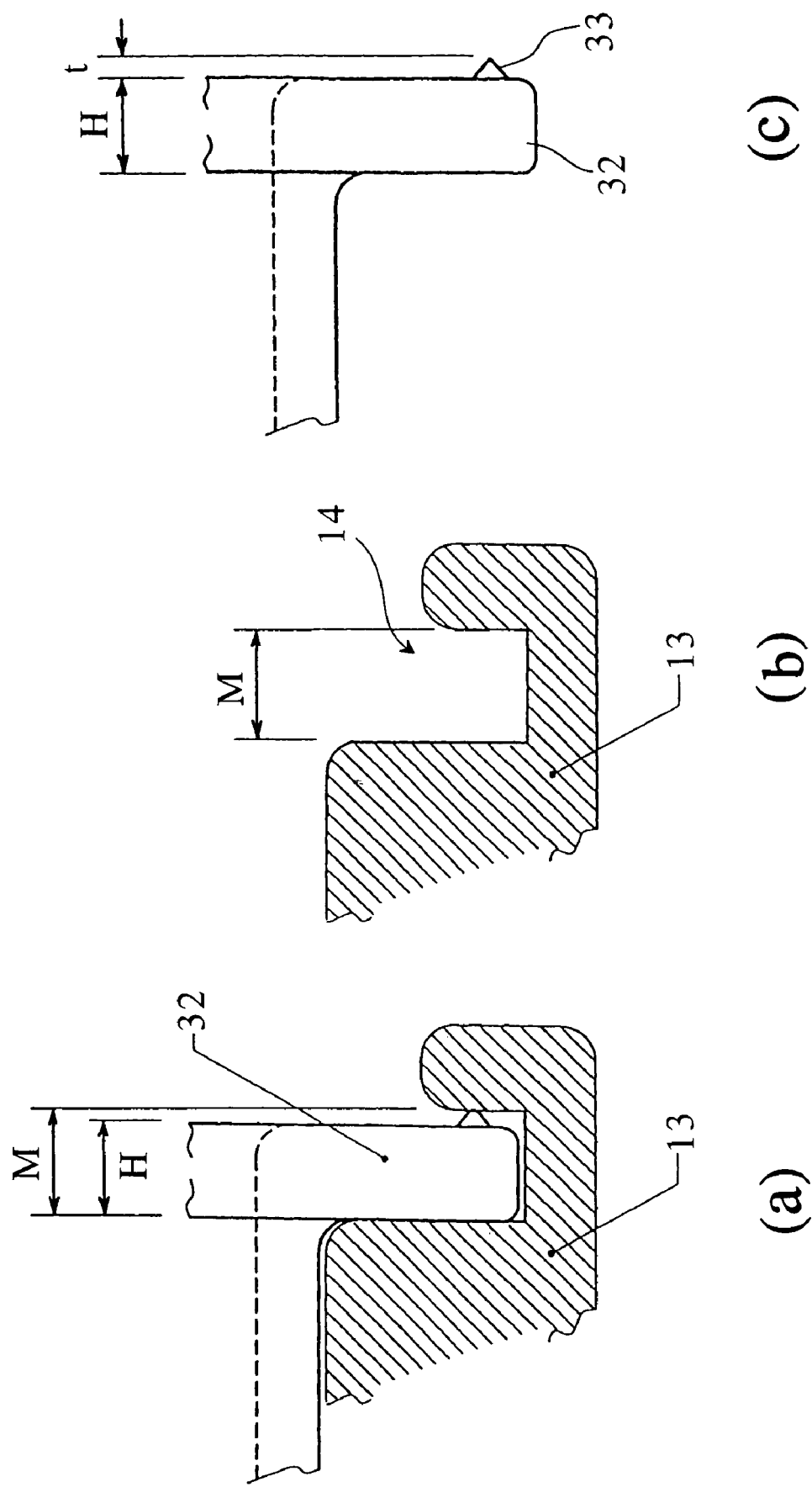
FIG. 2 is an enlarged view.

FIG. 1 shows a syringe barrel 31 mounted on a cylinder holder (adaptor 13). FIG. 2 (a) is an enlarged view of A part of FIG. 1, and shows fitting of a flange with a flange insertion groove. FIG. 2 (b) is an enlarged view of a flange insertion groove 14 of a cylinder holder 13, and FIG. 2 (c) is an enlarged view of a flange 32. For smooth mounting in use, the flange thickness H of a syringe barrel is smaller than the width M of a flange insertion groove. The difference between M and H can be appropriately selected also in view of accuracy of molding, and as the design value, for example, values of about 0.2 to 2 mm can be selected. As shown in FIG. 2 (c), the height t of a projection 33 provided in a flange 32 is so set that H+t is larger than M. Then, in inserting into the flange insertion groove, the tip of the projection is compressed and crushed, and just fitted together with the flange into the flange insertion groove. In this motion, due to elastic force of the compressed projection, the front surface of the flange is pressed to the front surface of the groove and fixed firmly.

The height "t" of the projection can be appropriately determined in view of the raw materials thereof and handling property of the projection. Though it is also possible to form the projection of the different material from that of the flange, it is usually preferable that the projection is integrally formed with the flange. The flange barrel is, usually, formed of a resin such as polypropylene and the like, and the adaptor is formed of ABS, polycarbonate and the like. Depending on selection of materials, a constitution may also be so formed that the cylinder holder side is compressed, however, when the above-mentioned materials are used, the projection of the syringe barrel is compressed. In this constitution, even if the tip of the projection is compressed and plastically deformed, firm fixing due to elasticity is obtained since compression force necessarily remains to a certain extent.

Therefore, it is usually preferable that H+t is larger than M by about 0.1 to 2.5 mm, particularly preferably by about 0.2 to 2.0 mm, and further, most preferably by about 0.3 to 1.5 mm.

Next, a further specific embodiment will be illustrated referring to drawings.

Embodiment A-1

Figure 3:
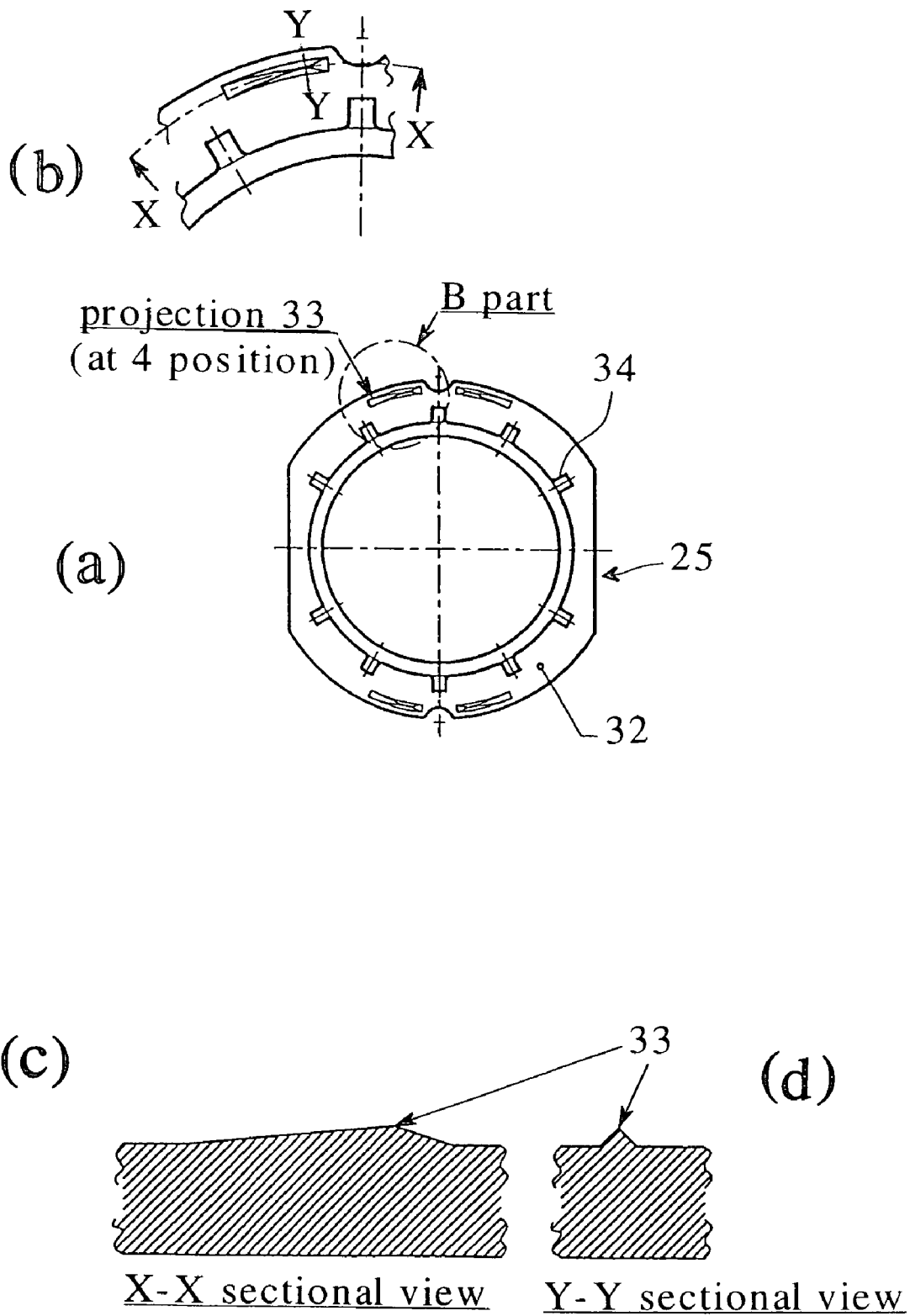

In an embodiment shown in FIG. 3, the projection 33 has a pyramid-like shape in which the bottom surface thereof is in the shape of a rectangle-like shape, the longer edge being along the circumferential direction of the flange, and moderate inclination is formed toward the tip. FIG. 3 (b) is an enlarged view of B-part in FIG. 3 (a), FIG. 3 (c) is an x-x sectional view along the circumferential direction in (b), and FIG. 3 (d) is a y-y sectional view along vertical direction to the x-x-direction. The size of the projection can be appropriately determined, and in the case of a syringe of 100 mL, for example, the x-x direction length of the bottom surface can be about 5 mm to 10 mm, the y-y direction length can be about 0.5 mm to 2.0 mm, and the height can be about 0.1 mm to 0.5 mm.

This syringe barrel is, like a conventional syringe barrel, inserted in a cylinder holder (adaptor) so that a flange cut part 25 is in vertical orientation, then, rotated by about 90° to be fixed for use, as shown in FIG. 15.

In this figure, projections 33 are provided at four positions of a flange 32, and the positions are so set that when a syringe barrel is mounted on a cylinder holder, the projection is not fitted into a flange insertion groove and when the syringe barrel is rotated, the tip of the projection 33 is fitted into the flange insertion groove while being compressed. By the moderate inclination along the circumferential direction, rotation can be effected smoothly to the fixing position without causing excessive lodge in the rotation.

In this example and the following examples, a reinforcing rib 34 is provided on the rear surface of a flange to prevent breakage of the flange, and this reinforcing rib 34 is provided on the inner peripheral side than the projection so that it is not fitted in the flange insertion groove.

Embodiment A-2

Next, in an embodiment shown in FIG. 4 ((a) rear side view, (b) C part enlarged view, (c) x-x sectional view), a plurality of conical projections 35a to 35d aggregate to a projection group 35. In this example, heights of the projections are controlled as follows: 35a<35b<35c>35d, and the projections are placed in relatively near positions, consequently, a merit is obtained that smooth rotation is possible as in the case of Embodiment A-1 in which inclination is made along the circumferential direction. It is preferable that the tip of the cone has round shape. In this configuration, for example, the diameter of the bottom face of the cone can be set same as the y-y direction length of Embodiment A-1, and distances between projections can be so controlled that the distance from the end to another end of all four projections is approximately the same as the x-x direction length of projections in Embodiment A-1. Also regarding to the height, respective projection heights can be appropriately controlled so that the height of 35c is approximately the same as that of the projection in Embodiment A-1. The number of the projections can be appropriately selected.

Embodiment A-3

Figure 5:
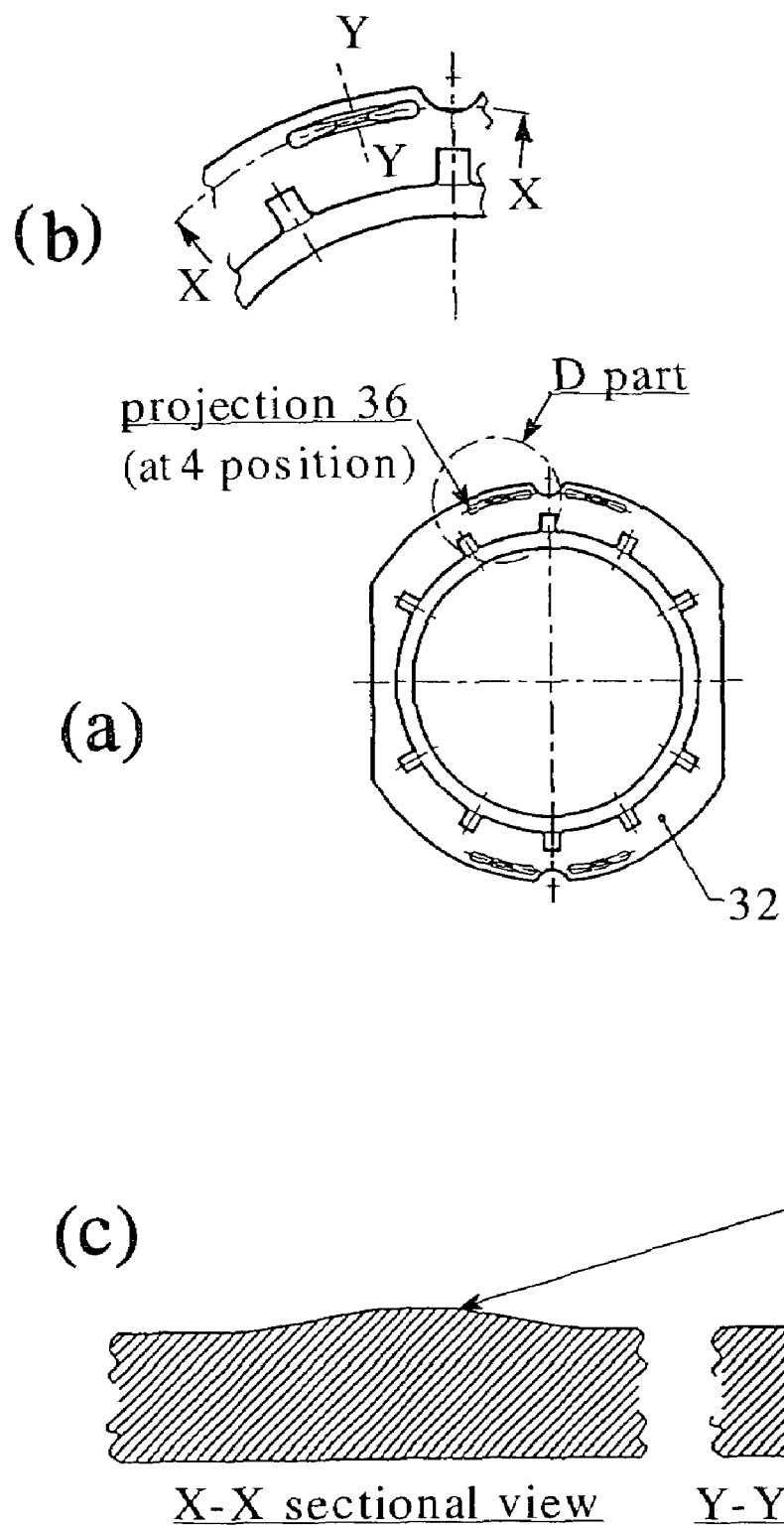

Next, in an embodiment shown in FIG. 5 ((a) rear side view, (b) D part enlarged view, (c) x-x sectional view), a projection 36 has a long cone-like shape in which the bottom face thereof is in the shape of an ellipse-like shape, the longer edge being along the circumferential direction of the flange, and moderate inclination is formed toward the tip. Further, the projection has a relatively flat part on the tip thereof. The flat part on the tip should not necessarily be flat completely. The size of the projection 36 can be selected according to Embodiment A-1.

Embodiment of Cylinder Holder Used Together with Syringe Barrel Having Projection As the cylinder holder used in combination with a syringe barrel as shown in Embodiments A-1 to A-3, usual cylinder holders (adaptor) having a flat surface to which the projection abuts as shown in FIG. 2 can be used. However, for enabling confirmation of fixation position by click feeling more stably and simultaneously, a concave portion may also be provided in a flange insertion groove of a cylinder holder.

FIG. 6 shows an examples of a cylinder holder used together with a syringe barrel shown in Embodiment A-1 (FIG. 3). Namely, as shown in FIG. 6 (a), a cylinder holder 40 has a concave portion 41, and is so formed that the position of the concave portion 41 coincides with the position of the projection 33 as shown in FIG. 6 (b) when syringe barrel is mounted and fixed at right use position (for example, FIG. 15 (c)). It is preferable, in this configuration, that the concave portion 41 is in the shape of a pyramidal cavity so that it is just engaged with the shape of the projection 33 as shown in FIG. 7 (sectional view vertical to paper surface in FIG. 6 (b)) since backlash does not occurs. In this configuration, it is preferable to modify appropriately the shape of the concave portion in view to a certain extent of deformation of projections occurring from the initiation of rotation to the arrival to the fixing position, further in view of elastic repulsion necessary for the fixation.

Also in the cylinder holder used for the syringe barrel in Embodiment A-2 (FIG. 4) and Embodiment A-3 (FIG. 5), a concave portion may advantageously be provided at a position corresponding to a projection at the fixing position, likewise.

FIGS. 8 and 9 show further other embodiments. In the embodiment of FIG. 8, the y-y direction (the same as the y-y direction defined in FIG. 3) section of a projection 38 is formed relatively vertically, and a concave portion of a cylinder holder 42 also has the corresponding sectional shape and formed in the shape of a groove. Also in this case, it is preferable that in the section watched along the circumferential direction (the same as the y-y direction defined in FIG. 3), inclination is provided and click feeling is obtained at the fixing position as in FIG. 7, for example. Further, in an embodiment of FIG. 9, though a concave portion of a cylinder holder 43 does not have a form completely engaged with the shape of a projection 39, in the y-y direction section, such a form can also be used. Also in this case, it is preferable that, when watched in the circumferential direction section, inclination is provided and click feeling is obtained at the fixing position.

Embodiment of Cylinder Holder Having Projection, and Syringe Barrel Used for the Same In the above-mentioned embodiments, projections are provided on a flange of a syringe barrel, however, a projection may also be provided in a flange insertion groove of a cylinder holder. In an example of a cylinder holder 45 (adaptor) shown in FIG. 10, projections 46 are provided on the inner wall surface of a groove (on the surface contacting with the flange rear surface). The projection can adopt the same form as in the case in which projections are provided on the flange surface as already described. In the example of FIG. 10, the shape of the projection is a pyramid-like shape like in Embodiment A-1.

When projections are provided on the cylinder holder side as in the present embodiment, the shape, size and the like of the projection can be set in the same manner as in the above-mentioned case in which projections are provided on the flange surface.

As the syringe barrel used together with a cylinder holder having such a projection, those having a flat flange as a conventional barrel can be used, and if a syringe barrel having a concave portion provided on the flange side is used, the fixing position can be confirmed more stably and simultaneously by click feeling, preferably. If the form of the concave portion on the flange side is so controlled to be engaged with the form of a projection on the cylinder holder side, backlash does not occur, preferably. A pyramidal cavity form is preferable for the pyramid-like projection as shown in FIG. 10.

Part II

In this part, description will be made for a syringe barrel and/or a cylinder holder where mechanism which restricts the position of the syringe barrel.

FIG. 20 is a view showing a syringe 130 in which a guide 131 is provided on a flange portion of the syringe, and (a-1) is a view showing state before syringe mounting, watched from the rear side of the syringe, (a-2) is a top view of a syringe and a cylinder holder, (b-1) is a view showing state after syringe mounting, watched from the rear side of the syringe, and (b-2) is a top view after syringe mounting.

In this embodiment, a guide 131 is provided on the rear surface of a flange 122. On the other hand, a groove 114 of a cylinder holder 111 has thickness for fitting of a flange, and this thickness (groove width) is smaller than the thickness including the guide 131. Therefore, as shown in FIG. 20 (a), the flange is fitted in the cylinder holder 111 while directing the guide 131 vertically. FIG. 20 (b) is a view showing the flange 122 fitted in the cylinder holder 111. In this example, an inner wall face 115 on the syringe side of the cylinder holder 111 has a straight line part, on the other hand, the guide 131 also has a straight line part, consequently, the syringe is fixed only at a position wherein flange cut parts 125 are placed at the upper location and at the lower location, thereby rotation thereof is inhibited. Resultantly, surface area by which the flange is held is large and pressure-receiving are during injection can be made large.

Further, a guide can be provided also on the front side of a flange. FIG. 27 is a view showing a syringe having a guide provided on the flange front side, watched from the tip side. As shown in this figure, by providing on the front side (syringe tip side) of the flange a guide 133 having such a thickness that at least the guide 133 is not fitted in a flange insertion groove, the syringe is mounted and fixed only when the flange cut surfaces 125 face the upper direction and the lower direction, as in the example of FIG. 20.

Regarding the guide, when it has a straight line part, mounting can be conducted more smoothly, however, even guides 135 composed of a plurality of dots as shown in FIG. 28 can provide positioning. Further, if the distance between two guides is made smaller at mounting side like guides 137 in an example of FIG. 29, mounting becomes easy.

FIG. 21 is a view showing an example of a syringe having positioning cut 141 provided on a flange cut part 125 of a flange 122, as a concave portion to be fitted in a positioning mechanism. On the other hand, on the cylinder holder side, a latch 142 is provided as a positioning mechanism to be fitted with the positioning cut 141, and a coil spring 143 is so provided that the latch is continuously pushed to the central direction. If rotation is effected manually by 90° after mounting in a cylinder holder in an orientation as shown in FIG. 21 (a), the flange is fixed at a position wherein the positioning cut 141 and the latch 142 are engaged (FIG. 21 (b)). In this point, click feeling is obtained, resultantly, credibility is improved since the setting position can be confirmed also by feeling. In the present invention, the term cylinder holder means a structure which has a groove, and a flange of a syringe is held by this groove to fix the syringe, and any of a case in which a cylinder holder is integrated with an injecting apparatus or a case in which it is dismountable like the adaptor and the like as shown in FIG. 13 may be adopted.

FIG. 22 shows an example in which positioning cut 151 is provided on an arc part 126 not on the flange cut part 125 of the flange 122. In such a case, it is preferable that a latch 152 is provided on the lateral side of a cylinder holder and a coil spring 153 is so provided that the latch 152 is pushed toward the central direction by the coil spring 153, as shown in FIG. 22 (b). If rotation is effected manually by 90° after mounting in a cylinder holder in an orientation as shown in FIG. 22 (a), the positioning cut 151 and the latch 152 are engaged (FIG. 22 (b)) to fix the flange. If latches 152 are provided on both side as shown in this figure, the fixing position is particularly stabilized, preferably.

In the example of FIG. 21, the positioning cut is provided on a flange cut part and in the example of FIG. 22, the positioning cut is provided on an arc part of a flange, however, it is also possible that a concave portion for positioning is separately provided in addition to a usual flange part. One example thereof is shown in FIG. 23. In this example, it may also be permissible that a flange reinforcing rib 161 is provided on the rear end surface of a flange, and a part of it is formed into a positioning part 162 to be fitted with a latch 163. Herein, the flange reinforcing rib 161 is formed by partially thickening the rear end surface of a flange as shown in FIG. 23 (c), and by this the flange is reinforced to prevent breakage thereof. Also in this example, if rotation is effected manually by 90° after mounting in a cylinder holder in an orientation as shown in FIG. 23 (a), the positioning part 162 and the latch 163 are engaged (FIG. 23 (b)) simultaneously with click feeling to fix the flange, like the example shown in FIG. 21.

FIG. 24 is a view showing an example in which a syringe having the positioning cut 151 provided on the arc part 126 of the flange 122 is used like the example shown in FIG. 22, on the other hand, a pawled blade spring 171 equipped with a pawl is provided on the cylinder holder side. After mounting in a cylinder holder while a flange cut part being directed vertically as shown in FIG. 24 (a), then, a syringe is rotated as in FIG. 24 (b), further as shown in FIG. 24 (c), the pawl 172 is fitted with the positioning cut 151 simultaneously with click feeling to provide fixing at a position of 90° rotation.

FIG. 25 is a view showing an example of an improved fixing method when the clamp as shown in FIG. 18 and FIG. 19 is used. The syringe of this example has a structure in which a guide 181 is provided on the flange front face of the syringe barrel 180, as shown in FIG. 25 (c). FIGS. 25 (a) and (b) show state of syringe mounting watched from A direction (from the tip direction) of FIG. 25 (c). When a syringe is pushed into a clamp 182 in open condition while flange cut surfaces 125 being directed toward the upper direction and lower direction as shown in FIG. 25 (a), the clamp 182 rotates around the fulcrum 183 and as shown in FIG. 25 (b), the upper part of the clamp closes and the syringe is mounted and fixed. Since the guide part is not fitted in the groove of the clamp due to the guide 181 provided, the syringe cannot be mounted at direction other than the direction wherein the flange cut surfaces are located at the upper position and the lower position. Consequently, pressure-receiving area in injection can be enlarged.

Also FIG. 26 is a view showing an example of an improved fixing method when the clamp as shown in FIG. 18 and FIG. 19 is used. Though in the syringe example shown in FIG. 25, the guide is provided on the front surface of a flange, in the example of FIG. 26, ribs are provided on the rear face of a flange of a syringe barrel 190 and the ribs are used as guides 191 as shown in FIG. 26 (c). FIGS. 26 (a) and (b) show state of syringe mounting watched from A direction (from the rear direction) of FIG. 26 (c). Likewise also in this case, when a syringe is pushed into a clamp 192 while flange cut surfaces 125 being directed toward the upper direction and lower direction as shown in FIG. 26 (a), the clamp 192 rotates around the fulcrum 193 and the syringe is mounted and fixed as shown in FIG. 26 (b). However, when the position of the flange cut surface is dislocated by the action of the guide 191, mounting is impossible.

The present invention has been illustrated by typical examples described above, however, the invention is not to be taken as limited to these examples, and modifications and variations may be made without departing from the spirit or scope of the invention. In the above-mentioned examples in the section Part II, pressure-receiving area is most large when flange cut surfaces are located at the upper position and the lower position, however, depending on the form of the cylinder holder, the flange cut surfaces should not necessarily be situated at the upper position and the lower position and variation can be made appropriately.

Further, it is preferable that a syringe of the present invention is used together with an injecting apparatus, particularly, an automatic injecting apparatus.

When a syringe has a guide which is engaged with a cylinder holder and restricts the mounting direction of the syringe to be mounted, that which is engaged with the syringe and can restrict the mounting direction of the syringe is used as the cylinder holder. Further, by co-use with an automatic injecting apparatus having a piston holder and a driving mechanism of the piston holder, as illustrated using FIGS. 11 and 13, even a chemical solution having high viscosity can be injected easily. Particularly, it can be suitably used for injection of various contrast agents as the chemical solution.

Regarding the structure, driving mechanism and the like of an automatic injecting apparatus, those which are public-known can be used.

Further, as the syringe of the present invention, syringes of generally spread type using a syringe barrel and a piston in combination are preferable, however, those of other types may be permissible providing they are syringes requiring positioning fixation of a flange direction.

Part III

In this part, description will be made for a syringe barrel having reinforcing structure.

FIG. 30 shows one example of a syringe barrel having a reinforcing rib provided on the rear surface of a flange, FIG. 30 (a) is a side view of a syringe barrel watched from the rear side, and FIG. 30 (b) is a side view of a syringe barrel around a flange part watched from the lateral side. Regarding to the orientation of the syringe barrel, the syringe tip side is the front direction as defined in FIG. 34. The reinforcing rib 210 has a concentric reinforcing part 211 and a radial reinforcing parts 212. The concentric reinforcing part 211 in the example of this drawing, the internal peripheral surface constitutes a part of the inner wall of the syringe barrel, and the thickness "d" is approximately the same as the thickness D of the syringe barrel. The thickness d may be, for example, from about 0.5 to 3-fold, preferably from about 0.5 to 2-fold, further preferably from about 0.7 to 1.5-fold based on the thickness D of the syringe barrel. The height $h_1$ of the concentric reinforcing part 211 can be appropriately set depending on the reinforcing strength required, and for example, can be set at from about 0.2 to 3-fold, preferably from about 0.4 to 2-fold of the thickness H of the flange 209.

Regarding to radial reinforcing part 212, though the length $p_1$ is set at about ½ of the width L of the flange 209 in the example of this figure, it can be appropriately selected in the range from ¼ to ⅓, preferably from ¼ to ⅔ of the width L of the flange. Also the width and number of the radial reinforcing part 212 can be appropriately set in view of the necessary strength. Further, a taper form wherein the height decreases toward the outside as shown in this figure is preferable from the standpoint of handling since lodging and the like do not occur easily, however, there occur no problem from the standpoint of reinforcement even if it is not made in tapered form.

FIG. 35 shows another example of the reinforcing rib. In this example, parts of radial reinforcing parts 212 like in FIG. 30 form a double rib 213 due to other reasons such as positioning and the like. All of the radial reinforcing parts may be formed into double ribs, or the number of the radial reinforcing parts which tend to receive force particularly may be increased and the width thereof may be increased.

FIG. 31 is one example of a syringe barrel having a double flange, FIG. 31 (a) is a side view of the syringe barrel watched from the rear side, and FIG. 31 (b) is a side view of the syringe barrel around a flange part watched from the lateral side.

The double flange is composed of two components, a flange 220a and a flange 220b, and a reinforcing rib 221 is provided therebetween. In the example of this figure, the reinforcing rib 221 can have same structure as the reinforcing rib exemplified in FIG. 30 except that the reinforcing rib 221 is composed of a concentric part and radial parts and the radial part is not in the form of taper. However, the reinforcing rib in this embodiment is not restricted to the structure of this example as far as the rib is formed in structures to connect two flanges for reinforcement.

FIG. 32 is one example of a syringe barrel having a thick part provided at the base part on the front surface of a flange, FIG. 32 (a) is a side view of the syringe barrel watched from the rear side, and FIG. 32 (b) is a side view of the syringe barrel around a flange part watched from the lateral side.

The thick part 231 at the base part is provided concentrically at the base of a flange 230. In this example, though the length $p_3$ along the radial direction of the thick part is set at about ½ of the width L of the flange 230, it can be appropriately selected, for example, in the range from ¼ to ¾, preferably from ¼ to ⅔ of the width L of the flange. Further, the thickness $h_3$ of the thick part 231 can be appropriately set depending on the reinforcing strength required, and for example, can be set at from about 0.2 to 2-fold, preferably from about 0.3 to 1.0-fold, further preferably from about 0.3 to 0.8-fold of the thickness H of the flange 230. Further, it is preferable that the angle of the thick part is cut as shown in the example of this figure.

FIG. 33 is one example of a syringe barrel in which a reinforcing part in the form of taper is provided on the front surface of a flange, FIG. 33 (a) is a side view of the syringe barrel watched from the rear side, and FIG. 33 (b) is a side view of the syringe barrel around a flange part watched from the lateral side (wherein, the left half is a sectional view).

In this example, the front part of a flange 240 constitutes a reinforcing part in the form of taper 241, and the end of the taper and the end of the flange coincide each other. In this example, cut out parts 242 are partially provided wherein the taper is not formed for positioning and other reasons, however, this is not essential for the present invention. The height h of the reinforcing part in the form of taper 241 can be appropriately set depending on the reinforcing strength required, and for example, can be set at from about 0.2 to 2-fold, preferably from about 0.3 to 1.0-fold, further preferably from about 0.3 to 0.8-fold of the thickness H of the flange 240.

As the raw materials of the syringe barrels shown in the above-mentioned examples, usual materials used for general syringe barrels can be used, and from the standpoint of the strength of a flange, those made of resins such as, for example, a polypropylene resin and the like are preferable, and the syringe barrel can be produced easily by known methods such as an injection molding method and the like.

When the structure of the present invention is compared with a structure in which the thickness of a flange is simply increased, it is known that simple increase in the thickness of a flange tends to left internal strain and cause distortion of shape, in injection molding. When the internal strain remains, strength can not be manifested corresponding to the thickness. In the case of distortion of shape, when a syringe piston is pushed, the position of a flange is not stabilized and positional displacement occurs. Then the pressure is concentrated only on a part of the flange and the flange tends to be broken, as schematically shown in FIG. 36. However, in the reinforcing structures of the present invention, approximately the same thickness as the thickness of a conventional flange and the thickness of a thick part of a conventional syringe barrel can be adopted, and in this case, strains does not remain and sufficient strength is obtained, further, stability is obtained also in the form thereof.

A method of holding a syringe barrel of the present invention by a groove of a cylinder holder and the like can be appropriately selected depending on the form. For example, when the reinforcing member is a reinforcing rib as shown in FIG. 30, particularly if a radial reinforcing part (not necessarily in the form of taper) is provided also onto peripheral parts, the reinforcing member can also be fixed together by a groove. FIG. 37 schematically shows holding by a groove. Such a reinforcing rib has improved accuracy in form as compared with a thick flange, additionally, contacts with the rear surface of a groove by relatively small area, consequently, close adherence is more improved and mounting at correct position is possible. However, in the case of a flange in which the thickness is simply increased, distortion of a plane on the rear side is large and backlash is large.

A syringe barrel of the present invention can be used for uses such as injection of liquid, and the like in various fields in combination with a usual piston, and for example, preferably used for injecting a chemical solution for medical use, particularly, it is preferably used for injecting a chemical solution having high viscosity such as a contrast agent requiring higher pressure for injection.

Further, it is also preferable that a syringe barrel of the present invention is used for a pre-filled syringe filled previously with a chemical solution such as a contrast agent and the like.

Part IV

In this part, description will be made for a syringe barrel and/or a cylinder holder where roughened surface is made.

Figure 38:
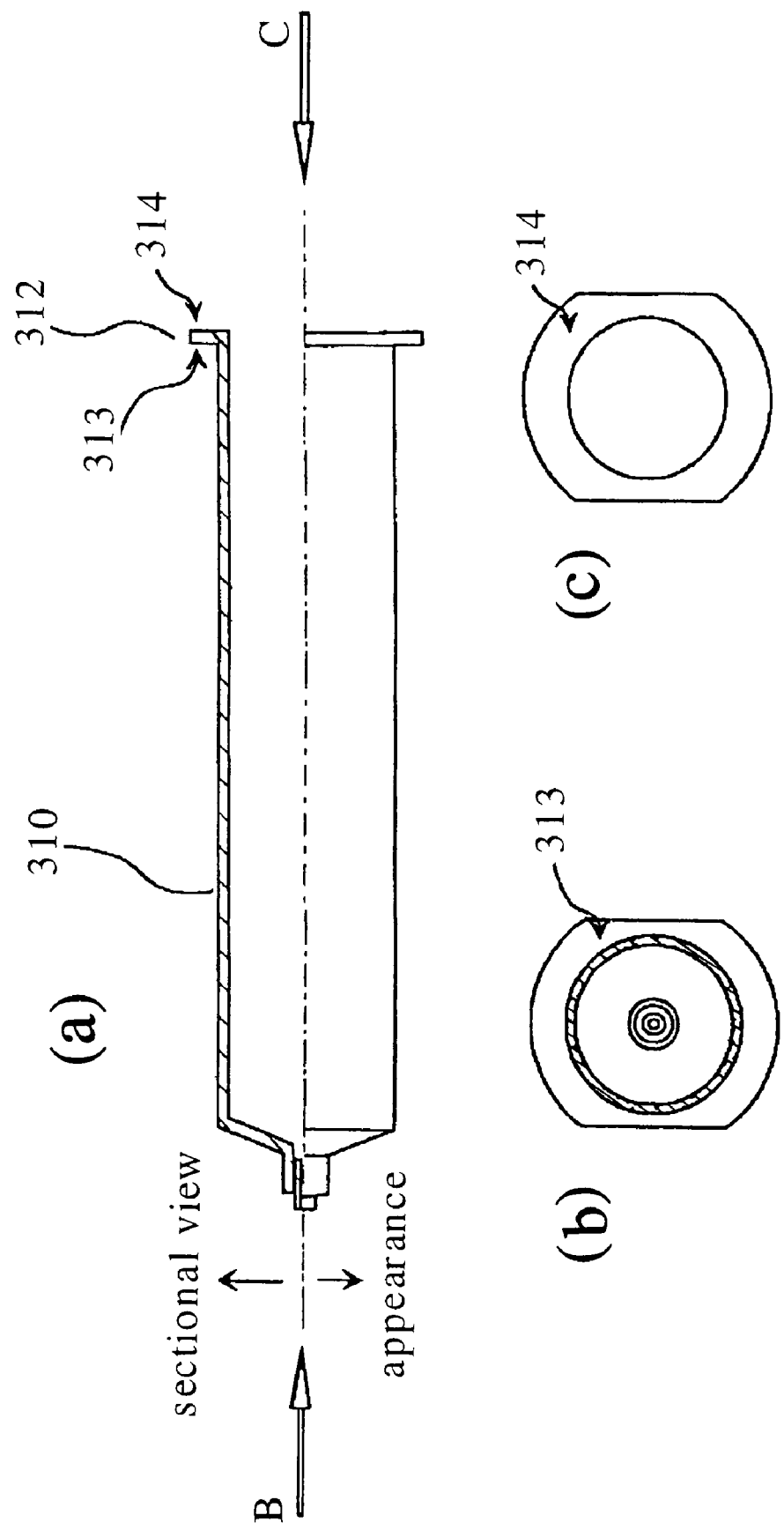

FIG. 38 shows one example of a syringe barrel of the present invention. The upper half of FIG. 38 (*a*) shows the section of a syringe barrel 310, and the lower half shows appearance thereof. FIG. 38 (*b*) is a side view of FIG. 38 (*a*) watched from B direction, namely, from the tip side of the syringe, and the front surface 313 of the flange is seen. On the other hand, FIG. 38 (*c*) is a side view of FIG. 38 (*a*) watched from C direction, namely, from the rear end side of the syringe, and the rear surface 314 of the flange 312 is seen.

In the present invention, at least one of the front surface and the rear surface of a flange is roughened. Roughening of the front surface 313 is effective to prevent breakage of a syringe in injecting liquid (in discharging liquid from a syringe). On the other hand, roughening of the rear surface 314 is effective to prevent breakage of a syringe in sucking liquid (in introducing liquid into a syringe).

In injecting liquid, large force is applied to a syringe piston 311 pulled out as shown in FIG. 40, therefore, moment around fulcrum, flange 312 is large, resultantly, displacement tends to occur, and simultaneously, large force tends to be applied to the fulcrum. Consequently, breakage of a syringe barrel is more significant in the case of injection. Therefore, it is preferable to roughen at least the front surface of a flange.

FIG. 39 shows one example of a cylinder holder (adaptor) of the present invention, and FIG. 39 (*a*) is a top view, FIG. 39 (*b*) is a side view watched from the rear side, FIG. 39 (*c*) is an enlarged view of the X-X section of FIG. 39 (*b*). For holding a syringe barrel by this cylinder holder 320, a flange is fitted in and fixed by a groove 321. In the cylinder holder of the present invention. At least one of a surface 322 contacting with the front surface of a flange and a surface 323 contacting with the rear surface of a flange is roughened. Like in roughening a flange surface of a syringe barrel, roughening of the surface contacting with the front surface of a flange is effective to prevent breakage of a syringe during injecting liquid (in discharging liquid from a syringe). On the other hand, roughening of the surface 323 contacting with the rear surface of a flange is effective to prevent breakage of a syringe in sucking liquid (in introducing liquid into a syringe). Also in this case, roughening of the surface 322 contacting with the front surface of a flange is effective to prevent breakage.

In the present invention, the extent of roughening can be appropriately selected in view of materials of a syringe barrel and cylinder holder and mutual combination thereof, and the like. For example, No. about 20 to 1500 (#20 to #1500), particularly No. about 50 to 800 (#50 to #800) is preferable, further, No. about 80 to 400 (#80 to #400) is preferable, in terms of the count of sand paper. The roughening pattern may be, for example, random such as the surface of sand paper, or regular. For example, convex-concave in the form of stripe may be used. In this case, it may be advantageous that approximately the above-mentioned roughening is formed along the direction crossing the stripe. In the case of regular roughening pattern, when a syringe barrel is set on a cylinder holder, it is preferable that the pattern is so provided that friction resistance along vertical direction is large.

In the roughening, whole of the front surface or the rear surface of a flange thereof may be roughened. Alternative, only a part of it may be roughened. Particularly when set on a cylinder holder, it is preferable that parts including a part contacting with a flange insertion groove are roughened.

As the raw material of the syringe barrel, usual materials in circulation can be used, and from the standpoint of the strength of a flange, those made of resins such as, for example, a polypropylene resin and the like are preferable. Further, the raw material of a cylinder holder is not particularly restricted, and metals may also be used, in addition to resins such as polycarbonate, ABS and the like.

A method of roughening a flange of a syringe barrel or a groove of a cylinder holder can be appropriately selected depending on materials. Specifically, the following methods and the like are listed.

(a) A method in which when a syringe barrel or a cylinder holder is molder, roughening is conducted simultaneously:

In this method, a syringe barrel or a cylinder holder is molded by using a mold (usually, metal mold) having a roughened surface. At least, a portion of the surface of the mold which forms the surface of a flange surface or a groove surface required to be roughened has a roughened surface. Thus, a syringe barrel or cylinder holder made of a resin is produced in simple production with high productivity by injection molding and the like.

(b) A method in which a flange surface or groove surface of a syringe barrel or cylinder holder manufactured is roughened mechanically:

In this method, a flange surface or groove surface of a syringe barrel or cylinder holder which has been molded can be mechanically roughened by file rubbing, punching by a needle, sand blast and the like.

(c) A method in which a roughened tape and the like are pasted on a flange surface or groove surface of a syringe barrel or cylinder holder manufactured:

In this method, a member such as a tape and the like having a roughened surface is separately prepared, and is affixed integrally to a flange surface or groove surface of a syringe barrel or a cylinder holder by using an adhesive, or by heat fusion and the like.

In using syringe barrels or cylinder holders as described above, it may be advantageous that at least one of them is roughened, and both of a syringe barrel and a cylinder holder may be roughened and combined for use.

A syringe barrel or cylinder holder of the present invention can be used in uses such as injection of liquid and the like in various fields, and for example, it is preferably used for injecting a chemical solution for medical use for example, and particularly, it is preferably used for injecting a chemical solution having high viscosity such as a contrast agent requiring high pressure for the injection. For example, a syringe barrel or cylinder holder of the present invention can be used without breakage of a syringe, even in use for injecting a chemical solution requiring an injection pressure of 2 Mpa or more, further, 2.5 Mpa or more.

Further, it is also preferable that a syringe barrel of the present invention is used as a pre-filled syringe which is previously filled with a chemical solution such as a contrast agent and the like.

On the other hand, a syringe piston of the present invention is one in which the rear end surface of a piston rod is roughened. In a usually syringe, the rear end of a piston rod constitutes a flange 331 as shown in FIG. 40, and in the present invention, the rear end surface 330 of this flange 331 is roughened.

A piston holder of the present invention is one in which a press surface contacting with the rear end surface of a syringe piston rod is roughened, and for example, in an automatic injecting apparatus of FIG. 11, a press surface 12 for pressing the rear end surface 330 of a piston rod is roughened. Usually, a piston holder has a press surface, and a clamp mechanism for holding a flange of a piston, and various embodiments are possible.

Raw materials, extent of roughening (roughness, area), roughening method, rough surface forming method and the like can be set according to the above-mentioned syringe barrel. Likewise, those of a piston holder can be set according to the above-mentioned cylinder holder.

These syringe piston and piston holder are also preferably used particularly for injecting chemical solution having high viscosity such as a contrast agent requiring high pressure, and use of a pre-filled syringe previously-filled with a chemical solution such as a contrast agent and the like is also preferable.

EXAMPLES

The following examples illustrate the present invention further in detail below.

Examples 1 to 3

In producing a mold for production of a cylinder holder holding a 100 mL syringe barrel, the mold surface of a part which forms the front surface of a cylinder holder was roughened by a sand blast method. By this mold, a cylinder holder was produced according to injection molding using a polycarbonate resin. The surface roughness of the front surface of a flange insertion groove was No. 100 (Example 1), No. 200 (Example 2) or No. 300 (Example 3) in terms of count of sand paper (#100, #200 and #300, respectively).

By using this cylinder holder, a 23 G butterfly needle was mounted on a syringe (internal diameter: 32 mm) of 100 mL capacity using a usual polypropylene syringe barrel in which the surface of a flange had not been roughened, and a pressure-resistance test was conducted using water as injection liquid. The results are shown in Table 1. In this test, breakage of the syringe and displacement of the flange such as raising from the right position did not occur even if injection was conducted at a high injection speed of 6 mL/sec and consequently the pressure increased to 28 kg/cm².

TABLE 1

| | Injection rate (mL/sec) | Pressure gage indication (MPa) | Remarks |
|---|---|---|---|
| Example 1 | 6 | 2.83 | Three continuous |
| | 6 | 2.88 | injection |
| | 6 | 2.86 | |
| Example 2 | 6 | 2.86 | Three continuous |
| | 6 | 2.88 | injection |
| | 6 | 2.83 | |
| Example 3 | 6 | 2.87 | Three continuous |
| | 6 | 2.79 | injection |
| | 6 | 2.83 | |

Comparative Examples

Cylinder holders were produced in the same manner as in Example 1 except that the surface of a mold in producing a cylinder holder was not roughened, and the same pressure-resistance test was conducted as in Example 1. The results are shown in Table 2.

TABLE 2

| | Injection rate (mL/sec) | Maximum pressure (Mpa) | Remarks |
|---|---|---|---|
| Comparative Example 1 | 3.5 | 1.80 | Injection rate is low |
| Comparative Example 2 | 4.0 | 2.14 | Raised and deviated from holder |
| Comparative Example 3 | 4.0 | 2.06 | Raised and deviated from holder |

TABLE 2-continued

| | Injection rate (mL/sec) | Maximum pressure (Mpa) | Remarks |
|---|---|---|---|
| Comparative Example 4 | 4.0 | 2.17 | Syringe barrel was broken |
| Comparative Example 5 | 4.0 | 2.25 | Syringe barrel was broken |
| Comparative Example 6 | 4.6 | 2.33 | Syringe barrel was broken |
| Comparative Example 7 | 4.0 | 2.33 | Syringe barrel was broken |

Example 4

The front surface of a flange of a usual 100 mL syringe barrel was roughened using sand paper. Since this operation was conducted manually, the condition of the roughened surface was not completely random, and is believed to be No. 100 to No. 300 (#100 to #300). A cylinder holder made of a usual polycarbonate resin in which the groove surface had not been roughened was used in the pressure-resistance test to obtain approximately the same results as in Example 1.

As described above, according to the present invention, including all aspects of the invention, a syringe barrel can be provided which is not easily broken even in injecting a solution having high viscosity such as a contrast agent at higher pressure.

Further, according to the present invention, a cylinder holder can be provided which does not cause breakage of a syringe even if it is a usual syringe.

What is claimed is:

1. An injection apparatus, comprising:
   a cylinder holder that comprises a flange insertion groove having a first surface and a second surface; and
   a syringe barrel, comprising a flange adapted to be held by said flange insertion groove so as to fix the syringe barrel, said flange having a front surface and a rear surface,
   wherein said first surface of the flange insertion groove contacts the front surface of the flange and the second surface of the flange insertion groove contacts the rear surface of the flange, wherein at least one of the front surface, the rear surface of the flange, the first surface of the flange insertion groove, and the second surface of the flange insertion groove has a random roughness pattern, and wherein the cross section of the roughened surface has a roughness equivalent to that of about No. 100 to 300 as expressed in terms of count of sand paper.

2. The injection apparatus according to claim 1, wherein the front surface of the flange is roughened.

3. An injection apparatus according to claim 1 or claim 2, further comprising:
   a syringe comprising said syringe barrel; and
   a chemical solution filled in the syringe.

4. The injection apparatus of claim 1, wherein the first surface of the flange insertion groove has the random roughness pattern.

* * * * *

UNITED STATES PATENT AND TRADEMARK OFFICE
CERTIFICATE OF CORRECTION

PATENT NO. : 7,695,457 B2  Page 1 of 1
APPLICATION NO. : 10/692090
DATED : April 13, 2010
INVENTOR(S) : Shigeru Nemoto It is certified that error appears in the above-identified patent and that said Letters Patent is hereby corrected as shown below:

Title page under the heading "Foreign Application Priority Data", Item 30, please delete "Feb. 2, 2000", and insert -- Feb. 2, 2001 --, therefor, At column 13, line 5, please delete "h", and insert -- $h_4$ --, therefor.

Signed and Sealed this
Fifteenth Day of February, 2011

David J. Kappos
*Director of the United States Patent and Trademark Office*